(12) United States Patent
Leung et al.

(10) Patent No.: US 11,712,304 B2
(45) Date of Patent: Aug. 1, 2023

(54) SYSTEMS AND METHODS FOR PERFORMING INTRAOPERATIVE SURFACE-BASED REGISTRATION AND NAVIGATION

(71) Applicant: 7D SURGICAL INC., Toronto (CA)

(72) Inventors: Michael K. K. Leung, Markham (CA); Adrian Mariampillai, Toronto (CA); Beau Anthony Standish, Toronto (CA); Peter Siegler, Toronto (CA); Victor X. D. Yang, North York (CA)

(73) Assignee: 7D Surgical ULC., Toronto (CA)

( * ) Notice: Subject to any disclaimer, the term of this patent is extended or adjusted under 35 U.S.C. 154(b) by 762 days.

(21) Appl. No.: 16/623,649

(22) PCT Filed: Jun. 21, 2018

(86) PCT No.: PCT/CA2018/050757
§ 371 (c)(1),
(2) Date: Dec. 17, 2019

(87) PCT Pub. No.: WO2018/232514
PCT Pub. Date: Dec. 27, 2018

(65) Prior Publication Data
US 2020/0197100 A1 Jun. 25, 2020

Related U.S. Application Data

(60) Provisional application No. 62/524,110, filed on Jun. 23, 2017.

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 17/7074* (2013.01);
(Continued)

(58) Field of Classification Search
CPC ..... A61B 34/20; A61B 34/25; A61B 17/7074; A61B 2017/00216; A61B 2017/564;
(Continued)

(56) References Cited

U.S. PATENT DOCUMENTS 9,119,670 B2  9/2015 Yang et al.
9,202,387 B2  12/2015 Gilboa
(Continued)

FOREIGN PATENT DOCUMENTS

CA        2961079 A1      3/2016
WO        2008103383 A1   8/2008
(Continued)

OTHER PUBLICATIONS

Rasoulian Abtin et al: "Feature-based multibody rigid registration of CT and ultrasound images of lumbar spine", Medical Physics, AIP, Melville, NY, US, vol. 39, No. 6, Jun. 1, 2012 (Jun. 1, 2012), pp. 3154-3166.
(Continued)

*Primary Examiner* — Molly Wilburn
(74) *Attorney, Agent, or Firm* — Hill & Schumacher

(57) ABSTRACT

Various example embodiments of the present disclosure provide systems and methods for performing image-guided navigation during medical procedures using intraoperative surface detection. A surface detection device is employed to obtain intraoperative surface data characterizing multiple surface regions of a subject. Pre-operative volumetric image data is registered to each surface region, providing per-surface-region registration transforms. In some example embodiments, navigation images may be generated intraop-
(Continued)

eratively based on the dynamic selection of a suitable registration transform. For example, a registration transform for generating navigation images may be dynamically determined based on the proximity of a tracked surgical tool relative to the surface regions. In an alternative example embodiment, multiple navigation images may be displayed, wherein each navigation image is generated using a different registration transform.

45 Claims, 21 Drawing Sheets

(51) Int. Cl.
  *A61B 34/10* (2016.01)
  *A61B 90/00* (2016.01)
  *A61B 17/70* (2006.01)
  *A61B 17/00* (2006.01)
  *A61B 17/56* (2006.01)

(52) U.S. Cl.
  CPC ............ *A61B 2017/00216* (2013.01); *A61B 2017/564* (2013.01); *A61B 2034/107* (2016.02); *A61B 2034/254* (2016.02); *A61B 2090/363* (2016.02); *A61B 2090/364* (2016.02); *A61B 2090/365* (2016.02); *A61B 2090/3983* (2016.02)

(58) Field of Classification Search
  CPC ........ A61B 2034/107; A61B 2034/254; A61B 2090/363; A61B 2090/364; A61B 2090/365; A61B 2090/3983; A61B 90/00; A61B 2034/2055; A61B 2090/373; A61B 2090/378; A61B 34/10
  See application file for complete search history.

(56) References Cited

U.S. PATENT DOCUMENTS

| | | | | |
|---|---|---|---|---|
| 2004/0097805 | A1* | 5/2004 | Verard | A61B 8/4254 600/428 |
| 2004/0215071 | A1* | 10/2004 | Frank | A61B 6/463 600/407 |
| 2008/0063301 | A1 | 3/2008 | Bogoni et al. | |
| 2008/0123927 | A1* | 5/2008 | Miga | A61B 90/36 382/131 |
| 2008/0269588 | A1 | 10/2008 | Csavoy et al. | |
| 2010/0054525 | A1 | 3/2010 | Gong et al. | |
| 2013/0279784 | A1 | 10/2013 | Gill et al. | |
| 2015/0371361 | A1* | 12/2015 | Kim | G06T 7/33 382/128 |
| 2016/0191887 | A1* | 6/2016 | Casas | H04N 13/366 348/47 |
| 2019/0298456 | A1* | 10/2019 | Leung | G06T 7/0012 |
| 2019/0307513 | A1* | 10/2019 | Leung | A61B 17/70 |
| 2019/0350658 | A1* | 11/2019 | Yang | A61B 6/032 |
| 2021/0128258 | A1* | 5/2021 | Quaid | A61B 34/37 |
| 2022/0202507 | A1* | 6/2022 | Siegler | A61B 90/37 |

FOREIGN PATENT DOCUMENTS

| | | |
|---|---|---|
| WO | 2011134083 A1 | 11/2011 |
| WO | 2015074158 A1 | 5/2015 |
| WO | 2016044934 A1 | 3/2016 |
| WO | 2017011892 A1 | 1/2017 |
| WO | 2017030915 A1 | 2/2017 |

OTHER PUBLICATIONS

Nagpal Simrin et al: "A multi-vertebrae CT to US registration of the lumbar spine in clinical data", International Journal of Computer Assisted Radiology and Surgery, Springer, DE, vol. 10, No. 9, Jul. 15, 2015 (Jul. 15, 2015), pp. 1371-1381.
International Search Report for PCT application PCT/CA2017/050770, dated Oct. 31, 2017.
Herring, Jeannette and Benoit Dawant, "Automatic Lumbar Vertebral Identification Using Surface-Based Registration", Journal of Biomedical Informatics 34, 74-87, (2001).
Hartkens, Thomas, "Intraoperative Spine Segment Guidance System", Prior Art Publishing, Prior Art Journal 2014 #02, pp. 226-227Feb. 3, 2014.
Irace, C Intraoperative Imaging for Verification of the Correct Level During Spinal surgery. Chapter 9 from Novel Frontiers of Advanced Neuroimaging, Edited by Kostas N. Fountas, Jan. 9, 2013.
International Search Report for PCT application PCT/CA2017/050807, dated Nov. 14, 2017.
International Search Report for PCT application PCT/CA2017/050830, dated Nov. 7, 2017.
International Search Report for the parent PCT application PCT/CA2018/050757, dated Oct. 2, 2018.

* cited by examiner

SYSTEMS AND METHODS FOR PERFORMING INTRAOPERATIVE SURFACE-BASED REGISTRATION AND NAVIGATION

CROSS-REFERENCE TO RELATED APPLICATION

This application is a National Phase application claiming the benefit of the international PCT Patent Application No. PCT/CA2018/050757, filed on Jun. 21, 2019, in English, which claims priority to U.S. Provisional Application No. 62/524,110, titled "SYSTEMS AND METHODS FOR PERFORMING INTRAOPERATIVE SURFACE-BASED REGISTRATION AND NAVIGATION" and filed on Jun. 23, 2017, the entire contents of which are incorporated herein by reference.

BACKGROUND

This disclosure relates generally to navigated medical and surgical procedures. More particularly, the present disclosure relates to systems and methods for performing registration between volumetric image data and intraoperative surface image data to support intraoperative navigation.

Many surgical interventions take place on anatomical targets which are composed of multiple rigid body (orthopedic) elements. For example, the spine is composed of multiple vertebrae, and joints (knee, hip, shoulder) are composed of two or more bones. When navigating surgical procedures involving these anatomies, motion between the multiple elements during procedures can create errors in navigation information displayed to the user.

SUMMARY

Various example embodiments of the present disclosure provide systems and methods for performing image-guided navigation during medical procedures using intraoperative surface detection. A surface detection device is employed to obtain intraoperative surface data characterizing multiple surface regions of a subject. Pre-operative volumetric image data is registered to each surface region, providing per-surface-region registration transforms. In some example embodiments, navigation images may be generated intraoperatively based on the dynamic selection of a suitable registration transform. For example, a registration transform for generating navigation images may be dynamically determined based on the proximity of a tracked surgical tool relative to the surface regions. In an alternative example embodiment, multiple navigation images may be displayed, wherein each navigation image is generated using a different registration transform.

Accordingly, in one aspect, there is provided a method of performing intraoperative registration between intraoperative surface data and pre-operative volumetric image data associated with a subject, the method comprising:

employing a surface detection device to obtain intraoperative surface data characterizing at least a first surface region and a second surface region of the subject;

processing the pre-operative volumetric image data to generate pre-operative surface data characterizing at least the first surface region and the second surface region of the subject;

spatially segmenting one or both of the intraoperative surface data and the pre-operative surface data within the first surface region and the second surface region;

performing registration between the intraoperative surface data and the pre-operative surface data, to obtain a first registration transform associated with the first surface region and a second registration transform associated with the second surface region; and intraoperatively generating and displaying navigation images by employing a selected registration transform to register the pre-operative volumetric image data to an intraoperative frame of reference, wherein the selected registration transform is dynamically and intraoperatively selected from at least the first registration transform and the second registration transform.

In another aspect, there is provided a method of performing intraoperative registration between a subject and pre-operative volumetric image data associated with the subject, the method comprising:

employing a surface detection device to obtain intraoperative surface data characterizing at least a first surface region and a second surface region of the subject;

processing the pre-operative volumetric image data to generate pre-operative surface data characterizing at least the first surface region and the second surface region of the subject;

spatially segmenting one or both of the intraoperative surface data and the pre-operative surface data within the first surface region and the second surface region;

performing registration between the intraoperative surface data and the pre-operative surface data to obtain a first registration transform associated with the first surface region and a second registration transform associated with the second surface region; and intraoperatively generating and displaying first navigation images and second navigation images in two different windows of a user interface, wherein the first navigation images are generated by employing the first registration transform to register the pre-operative volumetric image data to an intraoperative frame of reference, and the second navigation images are generated by employing the second registration transform to register the pre-operative volumetric image data to the intraoperative frame of reference.

In another aspect, there is provided a system for performing intraoperative registration between intraoperative surface data and pre-operative volumetric image data associated with a subject, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

controlling said surface detection subsystem to obtain intraoperative surface data characterizing at least a first surface region and a second surface region of the subject;

processing the pre-operative volumetric image data to generate pre-operative surface data characterizing at least the first surface region and the second surface region of the subject;

spatially segmenting one or both of the intraoperative surface data and the pre-operative surface data within the first surface region and the second surface region;

performing registration between the intraoperative surface data and the pre-operative surface data to obtain a first registration transform associated with the first surface region and a second registration transform associated with the second surface region; and intraoperatively generating and displaying navigation images by employing a selected registration transform to register the pre-operative volumetric image data to an intraoperative frame of reference, wherein the selected registration transform is dynamically and intraoperatively selected from at least the first registration transform and the second registration transform.

In another aspect, there is provided a system of performing intraoperative registration between a subject and pre-operative volumetric image data associated with the subject, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

controlling the surface detection subsystem to obtain intraoperative surface data characterizing at least a first surface region and a second surface region of the subject;

processing the pre-operative volumetric image data to generate pre-operative surface data characterizing at least the first surface region and the second surface region of the subject;

spatially segmenting one or both of the intraoperative surface data and the pre-operative surface data within the first surface region and the second surface region;

performing registration between the intraoperative surface data and the pre-operative surface data to obtain a first registration transform associated with the first surface region and a second registration transform associated with the second surface region; and intraoperatively generating and displaying first navigation images and second navigation images in two different windows of a user interface, wherein the first navigation images are generated by employing the first registration transform to register the pre-operative volumetric image data to an intraoperative frame of reference, and the second navigation images are generated by employing the second registration transform to register the pre-operative volumetric image data to the intraoperative frame of reference.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
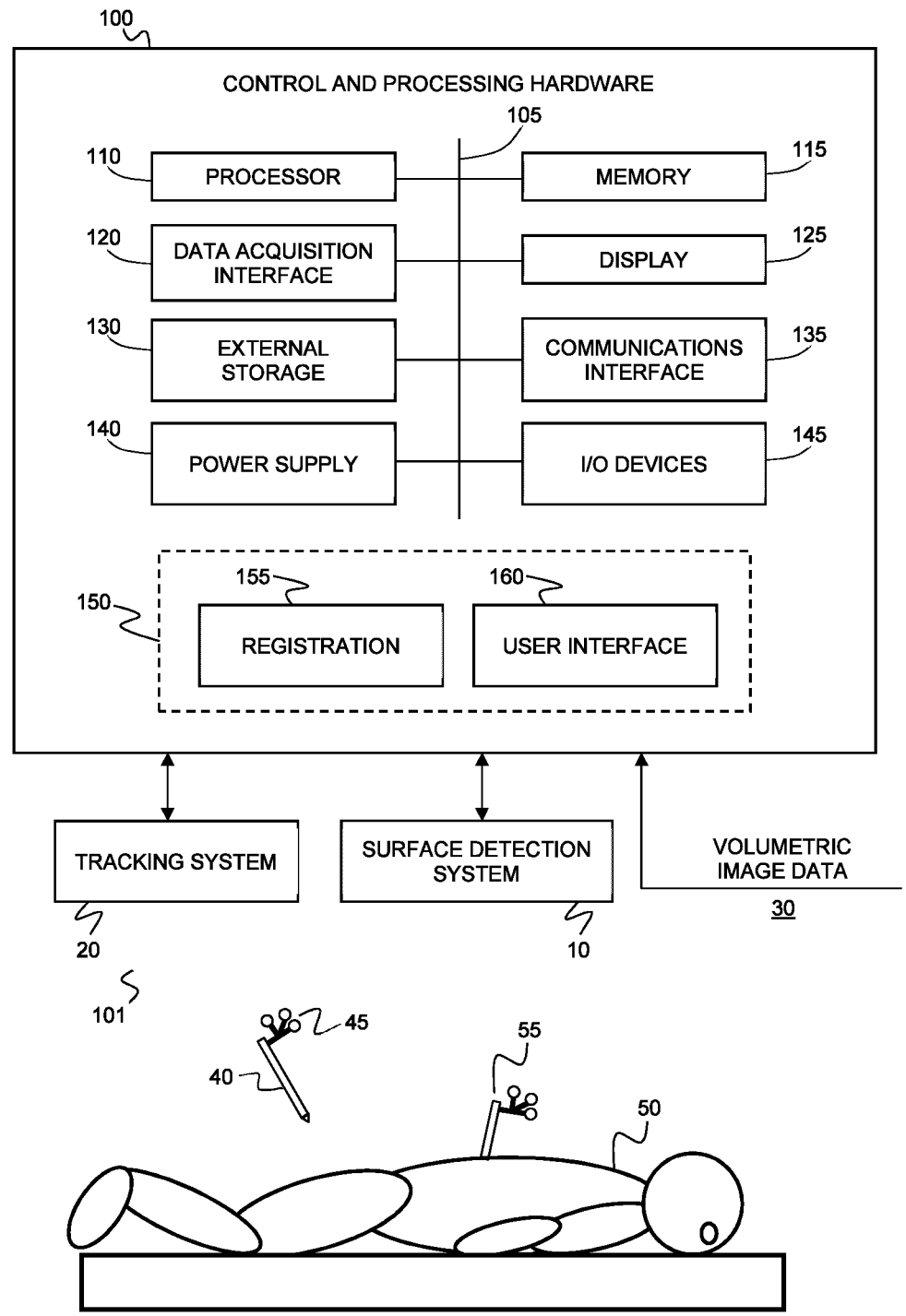
FIG. 1 shows an example system for performing intraoperative surface-based navigation of a surgical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the term "spinal orientation" refers to the six degrees of freedom in which spinal levels can move relative to other spinal levels. Alternatively, it is also referred to as the "orientation of the spine". As used herein, the six degrees of freedom of each individual spinal level is referred to by the term "position" for the translational component, and the term "orientation" is used for the rotational component.

As used herein, the phrase "intraoperative" refers to an event that occurs during a surgical procedure, including events before or after a phase of a surgical procedure. For example, an intraoperative measurement involving the surface topography of an exposed portion of the cranial anatomy may occur any time that cranial tissue is exposed, such as during an interventional phase of surgical procedure, and after the interventional phase, or prior to the interventional phase of a procedure.

Various example embodiments of the present disclosure provide systems and methods for performing image-guided navigation during medical procedures using intraoperative surface detection. According to conventional navigation methods, pre-operative image data is intraoperatively registered to an intraoperative frame of reference associated with a tracking system, and the transformed pre-operative image data is displayed on a user interface, along with intraoperatively tracked medical tools.

When performing navigation based on surface detection, pre-operative volumetric data is processed to generate pre-operative surface data associated with an anatomical region of interest, and the pre-operative surface data is registered to intraoperative surface data measured via a surface detection system. The surface registration provides a registration transform that relates the pre-operative volumetric image data from the pre-operative frame of reference to an intraoperative frame of reference associated with the surface detection system. A calibration transform is then employed to relate the intraoperative frame of reference associated with the surface detection system to the frame of reference of a tracking system, thereby facilitating the display of the volumetric image data and tracked surgical tools during navigation.

After performing registration, it may be beneficial to compensate for subsequent global changes in the intraoperative patient position and patient orientation. Such compensation can be achieved, for example, using an intraoperatively tracked reference frame that is secured to the patient. By intraoperatively tracking changes in the position and orientation of the tracked reference frame, the registration of the pre-operative volumetric image data to the intraoperative frame of reference of the tracking system can be dynamically adjusted to account for patient motion.

Surface-based navigation may be employed, for example, to facilitate intraoperative navigation during spinal surgical procedures, based on the detection of intraoperative surface image data associated with an exposed spinal level. In conventional surface-based spinal navigation, registration is performed for a single selected spinal level of interest, resulting in a single registration transform between the pre-operative surface data and intraoperative surface data associated with a single selected spinal level. As a consequence of this local registration that is specific to a single selected spinal level, navigation accuracy can be maintained at the selected spinal level, because the selected spinal level consists of a single rigid body (e.g. a solid vertebrae).

As noted above, a tracked reference frame can be used to compensate for global intraoperative changes in the position and orientation of the spine. However, changes in local positions and orientations of the spinal levels are not compensated by such a tracked reference frame. Such changes may occur, for example, due to a spinal intervention, such as the use of screws and rods to correct for a spinal deformity or pathology. Accordingly, it can be readily understood that when navigation of multiple spinal levels is required, a single registration transform (between multiple levels of the spine from the intraoperative surface data and preoperative volumetric data) will not necessarily be accurate across multiple spinal levels. For example, inaccuracies may even exist for spinal levels immediately adjacent to the selected spinal level.

The accuracy of a single registration transform, when applied to multiple spinal levels, degrades when there are discrepancies between the local intraoperative spinal orientation and the local preoperative spinal orientation, and the inaccuracy typically worsens as the number of spinal levels are increased. For example, Uehara et al. have shown that pedicle screw perforation rates are influenced by distance from the tracked reference frame in multi-level registration using a CT-based navigation system in the setting of scoliosis [Uehara M1, Takahashi J2, Ikegami S1, Kuraishi S1, Shimizu M1, Futatsugi T1, Oba H1, Kato H1, Spine J. 2016 Oct. 21. pii: S1529-9430(16)31034-8. doi: 10.1016/j.spinee.2016.10.019].

In order to avoid this inaccuracy, registration can be independently performed for each relevant spinal level during the medical procedure. For example, when a spinal procedure involving multiple spinal levels is to be performed, surface-based registration may be performed, on a per-level basis, separately and sequentially during the medical procedure, with only a single per-level registration transform employed at a time. For example, if the surgical procedure begins with a first spinal level, a single-level registration transform may be initially obtained and employed for the first level, and this first registration transform may then be employed to generate navigation images. Later, when the surgical procedure involves the second level, re-registration is performed to provide a new surface-based registration transform for the second level, and this second registration transform is employed to generate navigation images. This sequential process of registration results in a registration modality in which only a single registration transform is available and utilized at any given time during navigation of the surgical procedure.

The recommended surface-based navigation practice is therefore disadvantageous in that only a single spinal level is registered at any given time during the medical procedure, and navigation is therefore only accurate in a local region associated with a given spinal level. Moreover, this practice requires that registration be performed multiple times during the medical procedure, with a new registration being performed each time a new spinal level is encountered during the surgical plan. This need for multiple re-registration steps disrupts clinical workflow and leads to increased expense due to the time delays involved in each registration step.

Accordingly, in contrast to the recommended practice of separately and sequentially performing registration to individual rigid bodies of patient anatomy (e.g. individual spinal levels), various example embodiments of the present disclosure provide solutions whereby rigid body elements having independent positional and orientational degrees of freedom are independently registered and tracked, thereby maintaining accuracy in the presence of both global motion and local relative motion of the rigid bodies.

Various example embodiments of the present disclosure may additionally or alternatively be applied to navigated procedures that do not necessarily involve multiple rigid bodies separated by a joint, but involve large anatomical bodies (anatomical elements), such as the cranium. For example, although conventional cranial navigation methods employ a single large global transformation to register the patient to the pre-operative volumetric image data, in some instances, the regions where the procedure will take place are at or within selected sub-regions of the cranium (specific locations within the large anatomical body of the cranium). In such cases, it may be advantageous to perform multiple independent registrations locally at, adjacent to, or within these sub-regions independently to achieve maximum navigational accuracy at each sub-region.

Accordingly, unlike the surface-based navigation methods described above, some example embodiments of the present disclosure facilitate the dynamic selection of a suitable registration transform from a plurality of registration transforms that correspond to different intraoperatively exposed surface regions (e.g. different anatomical rigid bodies). The generation of multiple registration transforms that are accurate in different spatial regions enables the dynamic selection, during a medical procedure, of a registration transform that is most appropriate for the current phase of the medical procedure.

Furthermore, in some example embodiments, intraoperative surface detection of multiple surface regions (e.g. multiple anatomical bodies with independent degrees of freedom) is repeated during the medical procedure, and the multiple registration transforms are re-calculated and thus intraoperatively updated. This repeated updating of the multiple registration transforms may be particularly beneficial in applications involving the navigation of surgical procedures involving multiple rigid body elements having independent degrees of freedom, where the repeated updating of the multiple registration transforms accounts (compensates) for relative motion between the multiple rigid body elements during the procedure. The continuous updating of the multiple registration transforms is performed by repeatedly acquiring additional surface data (e.g. structured light images) and re-registering each rigid body element independently. In one example implementation, the updating of the registration transforms can be performed automatically (e.g. in the absence of user intervention or user input, such as in the absence of user input specifying updated fiducial points) if the motion between any two time points is relatively small, where the previous registration transform are employed to respectively act as in initial estimates for the calculation of the updated registration transforms.

Referring now to FIG. 1, an example system is shown for performing intraoperative surface-based navigation of a surgical procedure according to various example embodiments of the present disclosure. The example system includes a surface detection system 10 that is operably interfaced with control and processing hardware 100. The surface detection system 10 may be any suitable system for detecting, measuring, imaging, or otherwise determining the surface topography of one or more objects (such as, but not limited to, a region of an exposed spine of a patient 50) using optical radiation or sound waves (e.g. ultrasound). Non-limiting examples of suitable optical devices include laser range finders, photogrammetry systems, and structured light imaging systems, which project surface topography detection light onto a region of interest, and detect surface topography light that is scattered or reflected from the region of interest. The detected optical signals can be used to generate surface topography datasets consisting of point clouds or meshes. Other examples using sound waves for determining surface topography can include ultrasonography.

The example system may also include a tracking system 20, which may be employed to track the position and orientation of one or more medical instruments 40. The medical instrument 40 is shown having fiducial markers 45 attached thereto, and passive or active signals emitted from the fiducial markers 45 are detected by the tracking system 20 (e.g. a stereoscopic tracking system employing two tracking cameras). In an alternative example embodiment, the position and orientation of a medical instrument may be tracked via the surface detection subsystem 10, such as a structured light detection system, that is employed to detect the surface profile of at least a portion of the medical instrument, or structure attached thereto, and to determine the position and orientation of the medical instrument via comparison of the detected surface profile with a known surface profile.

As also shown in FIG. 1, a tracked reference frame 55 (e.g. a clamp with fiducial markers provided thereon or attached thereto) may be attached to the patient and may be tracked by the tracking system 20. Such a tracked reference frame 55 may be employed for image guided surgeries.

FIG. 1 also illustrates an example implementation of control and processing hardware 100, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 1 is illustrative of a non-limiting example embodiment, and is not intended to be limited to the components shown. Furthermore, one or more components of the control and processing hardware 100 may be provided as an external component that is interfaced to a processing device. For example, as shown in the figure, one or both of the surface detection system 10 and the tracking system 20 may be included as a component of control and processing hardware 100, or may be provided as one or more external devices.

Although only one of each component is illustrated in FIG. 1, any number of each component can be included in the control and processing hardware 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing hardware 100 may include many more or less components than those shown.

Control and processing hardware 100 may be implemented as one or more physical devices that are coupled to processor 110 through one of more communications channels or interfaces. For example, control and processing hardware 100 can be implemented using application specific integrated circuits (ASICs). Alternatively, control and processing hardware 100 can be implemented as a combination of hardware and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via hardware logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of hardware and/or software.

The control and processing hardware 100 is programmed with subroutines, applications or modules 150, that include executable instructions, which when executed by the one or more processors 110, causes the system to perform one or more example methods described in the present disclosure. Such instructions may be stored, for example, in memory 115 and/or other internal storage. In particular, in the example embodiment shown, registration module 155 includes executable instructions for registering segmented surface data (obtained from the volumetric image data 30) with intraoperative surface data that is obtained using the surface detection system 10, for enabling the dynamic selection of a suitable registration transform from a set of registration transforms associated with different surface regions. In the example application of spinal procedures, the registration module 155 may also be employed for computing inter-level registration transforms between adjacent levels in the volumetric frame of reference, as per some of the example embodiments described below. The navigation user interface module 160 includes executable instructions for displaying a user interface for displaying navigation images according to the dynamically selected registration transform.

As described above, surgical procedures involving the spine may involve a plurality of spinal levels, and the aforementioned method of separately and sequentially calculating a registration transform for each relevant spinal level can have many associated drawbacks. In contrast to the aforementioned methods of performing surface-based navigation, many example embodiments of the present disclosure facilitate the dynamic selection and use of a suitable registration transform from a plurality of registration transforms that correspond to different intraoperatively exposed surface regions (e.g. different spinal levels). The generation of multiple registration transforms that are accurate in different spatial regions enables the dynamic selection, during a medical procedure, of a registration transform that is appropriate for the current phase of the medical procedure.

Figure 2A:
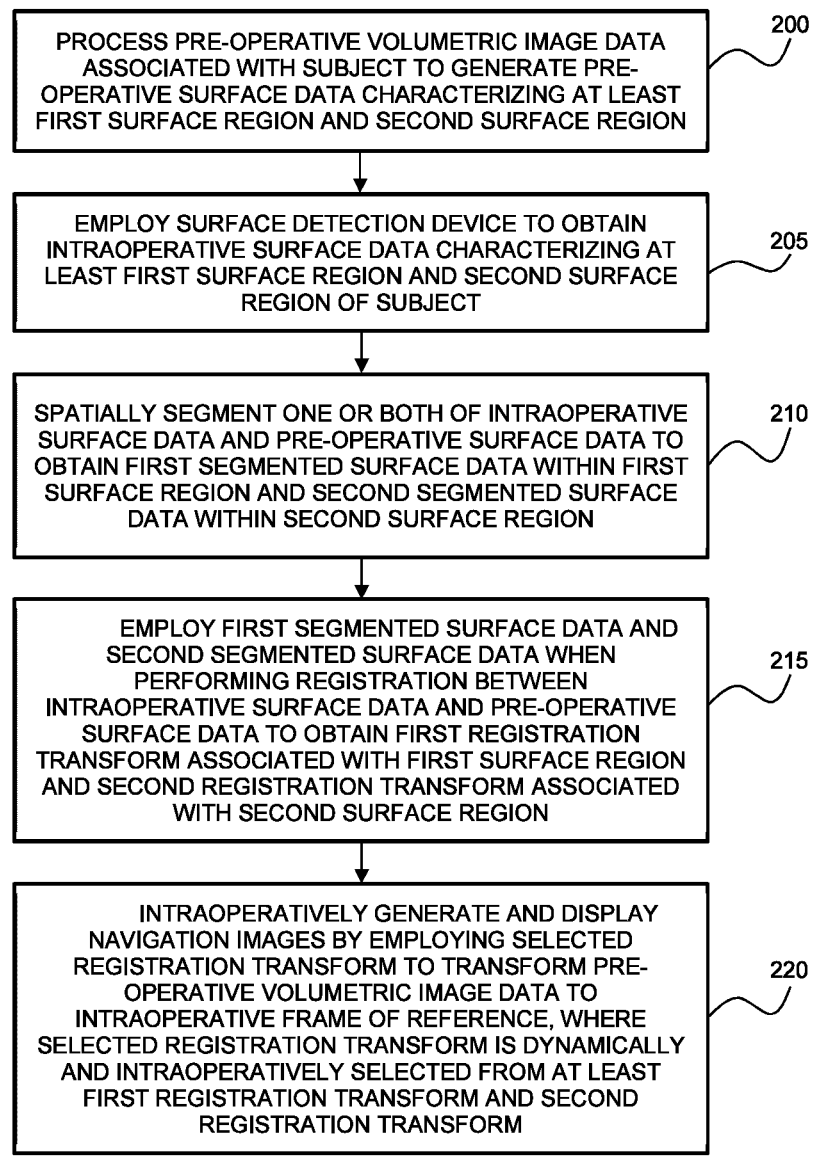
FIG. 2A is a flow chart illustrating an example method for generating surface-based navigation images for image-guided navigation of a medical procedure based on the calculation of multiple registration transforms associated with different surface regions, and the dynamic intraoperative selection of a suitable registration transform for the generation of navigation images.

Referring now to FIG. 2A, an example method is illustrated for generating surface-based navigation images for image-guided navigation of a medical procedure based on the calculation of multiple registration transforms associated with different surface regions, and the dynamic intraoperative selection of a suitable registration transform for the generation of navigation images.

Figure 3A:
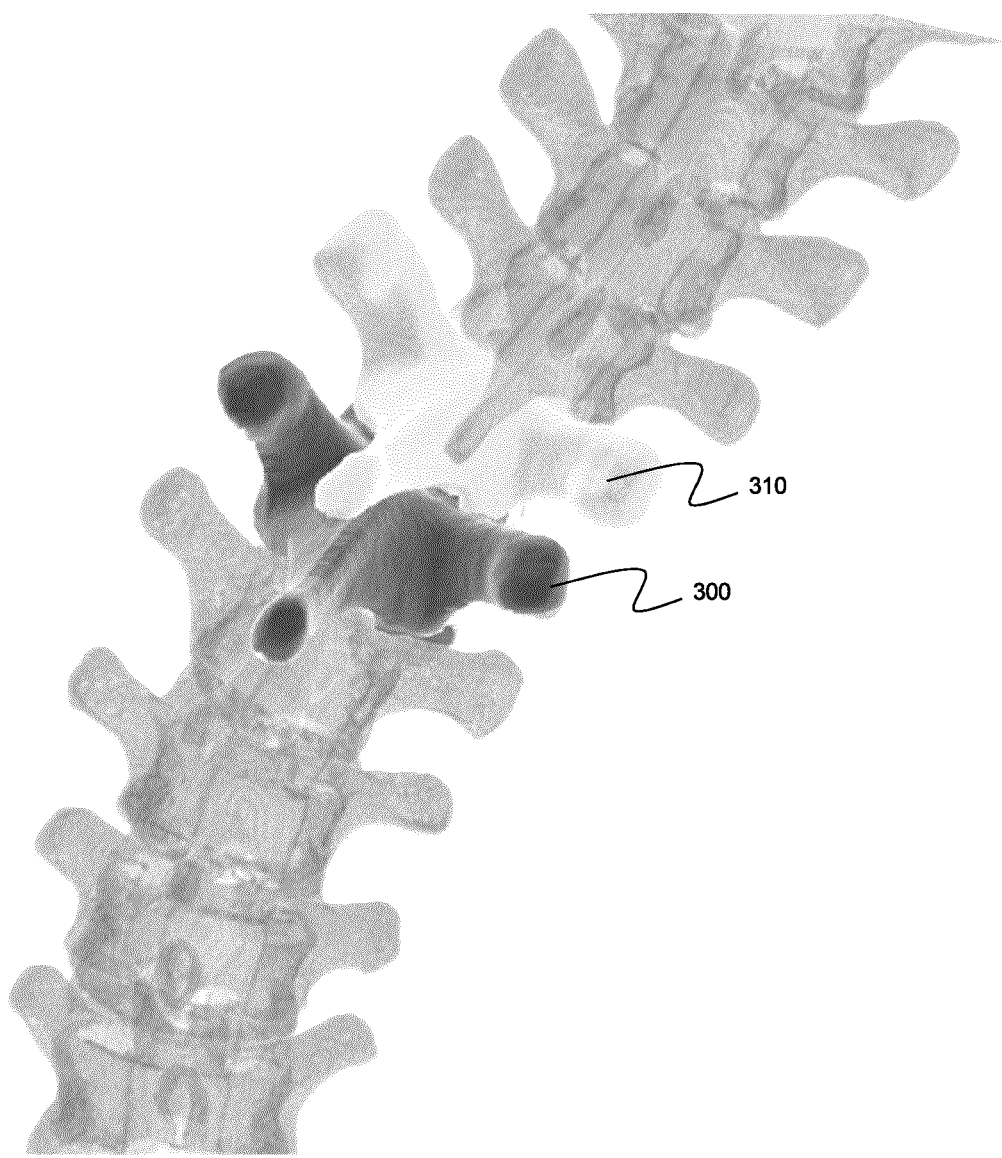
FIG. 3A shows an example of preoperative surface data characterizing two surface regions (two different spinal levels) of a subject.

As shown at step 200, the pre-operative volumetric image data associated with the subject is processed to generate pre-operative surface data characterizing at least the first surface region and the second surface region of the subject. An example of such a surface is shown in FIG. 3A, in the non-limiting example of a spinal procedure. FIG. 3A shows a multi-level surface image of the spine, that includes many spinal levels. In the present example, a planned procedure includes two levels—a first level 300 (a first surface region) and a second level 310 (a second surface region). The pre-operative surface shown in FIG. 3A, characterized by associated pre-operative surface data, resides in the volumetric frame of reference that is associated with the volumetric image data.

The pre-operative surface data may be generated according to a wide variety of methods. One example involves the selection of a bone threshold and generating an isosurface using the marching cubes algorithm from the volumetric image data. Another example is to construct an isocontour from each 2D slice of a volumetric image data based on a bone threshold, and stitching the slices together into a 3D surface.

In step 205 of FIG. 2A, a surface detection device (such as, but not limited to, a structured light surface detection device or system) is employed to obtain intraoperative surface data characterizing at least the first and second levels 300 and 310 (corresponding to the first surface region and the second surface region of the subject). It is noted that step 200 need not be performed prior to step 200.

Figure 3B:
FIG. 3B shows an example of intraoperative surface data detected using a structured light detection system, showing surface data from two surface regions (the two different spinal levels of FIG. 3A).

FIG. 3B shows an example of intraoperative surface data detected using a structured light detection system, in which the intraoperative surface data can be clearly seen to include a first surface region 300 corresponding to a first spinal level and a second surface region 310 corresponding to a second spinal level. The intraoperative surface data may be obtained in a single scan or image, such that a single intraoperative surface topography dataset is obtained including multiple spinal levels in the field of view. Alternatively, the intraoperative surface data may be obtained using two or more surface topography measurements, such that each measurement pertains to one or more spinal level.

According to step 210, at least one of the intraoperative surface data and the pre-operative surface data is spatially segmented within the first and second surface regions, thereby generating first and second segmented surface data. This spatial segmentation is useful in removing extraneous surface data, so that the surface registration process employs surface data that is local to the first surface region and the second surface region, thereby improving the accuracy and efficiency of the registration process. In one example implementation, both the intraoperative surface data and the pre-operative surface data are spatially segmented within the first and second surface regions (in the respective intraoperative and pre-operative frames of reference), producing first segmented intraoperative surface data and first segmented pre-operative surface data that are associated with the first surface region, and second segmented intraoperative surface data and second segmented pre-operative surface data that are associated with the second surface region.

In another example embodiment, only one of the intraoperative surface data and the pre-operative surface data is spatially segmented within the first and second surface regions (in the respective intraoperative and pre-operative frames of reference). For example, in one example implementation, only the intraoperative surface data is segmented, thereby producing first segmented intraoperative surface data that is associated with the first surface region, and second segmented intraoperative surface data that is associated with the second surface region. In another example implementation, only the pre-operative surface data is segmented, thereby producing first segmented pre-operative surface data that is associated with the first surface region, and second segmented pre-operative surface data that is associated with the second surface region.

An example of segmented pre-operative surface data is shown in FIG. 3A, where the segmented surface data for the first level 300 and the segmented surface data for the second level 310 are shown in different shades. The segmentation of the pre-operative surface data may be performed according to any suitable method. For example, one or more of volumetric fiducial points may be employed to initiate surface segmentation of a given level. The volumetric fiducial points associated with a given spinal level may be provided via manual input (e.g. as input received from a user or operator), or automatically generated, as described in further detail below.

Non-limiting examples of surface segmentation methods include non-template-based methods and methods which utilize anatomical shape models. Non-template-based methods can utilize geometrical properties, such as connectivity, surface normals, and curvatures to determine the boundary of the segmented region, or statistical properties, such as variance from nearby neighboring points on the surface. Methods based on anatomical shape models can utilize a pre-computed atlas (e.g. of vertebra in the case of a spinal procedure) as a template to perform the segmentation. Both classes of method can also be used in combination. In all these methods, one or more volumetric fiducial points can serve as a seed point to initialize the segmentation process. Alternatively, for segmentation methods which are fully automatic and operates on the entire volumetric data (which are usually based on anatomical atlases), one or more volumetric fiducials can be used to tag the anatomical regions or bodies (e.g. spinal levels) of interest.

Referring again to FIG. 2A, as shown at step 215, the first segmented surface data and the second segmented surface data (wherein one or both of the intraoperative surface data and the pre-operative surface data are segmented, as described above) are employed to separately register the intraoperative surface data and the pre-operative surface data within the first surface region and the second surface region, thereby obtaining a first registration transform associated with the first surface region and a second registration transform associated with the second surface region. For example, in the context of the example navigated spinal surgical procedure described above, a first registration transform is computed that is specific to (and locally accurate to) the first spinal level, and a second registration transform is computed that is specific to (and locally accurate to) the of second level.

Each registration may be initially performed as an initial registration based on correspondence, at each respective surface region, between per-region volumetric fiducial points and respective per-region intraoperative fiducial points. The per-region intraoperative fiducial points associated with a given surface region may be provided via manual input (e.g. as input received from a user or operator), or automatically generated, as described in further detail below. After generating respective initial registrations for each surface region, a surface-to-surface registration may then be performed for each region, between the segmented surface data and the intraoperative surface data, thereby obtaining region-specific registration transforms, as shown at step 215 of FIG. 2A. The registration transforms respectively map, for each region, the segmented surface in the pre-operative volumetric frame of reference to the intraoperative surface data.

Figure 3C:
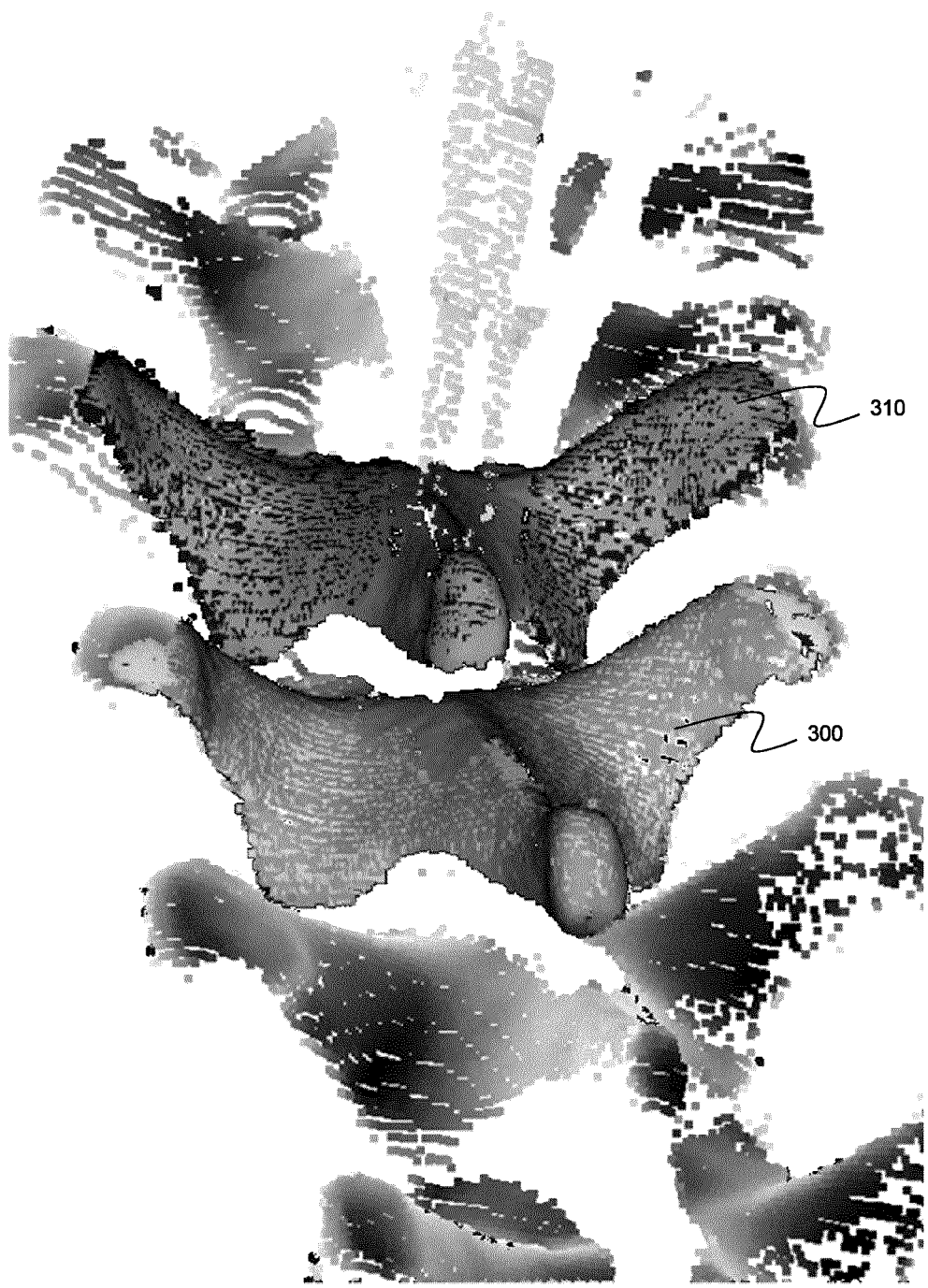
FIG. 3C illustrates registration of the pre-operative surface data to the intraoperative surface data, showing the close conformal correspondence of both datasets in both surface regions (corresponding the two different spinal levels).

FIG. 3C illustrates registration of the pre-operative surface data to the intraoperative surface data of the present example, showing the close conformal correspondence of both datasets in both the first surface region corresponding to the first level 300 and the second surface region corresponding to the second level.

It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

In the example case in which the different surface regions correspond to different anatomical bodies that have independent spatial degrees of freedom, the information for independent registration of the different surface regions can be obtained based on the determination of the intraoperative orientation of the different anatomical bodies. Example methods for the determination of the intraoperative orientation of a plurality of anatomical bodies (such as a plurality of spinal joints) are described in U.S. Provisional Patent Application No. 62/358,124, titled "SYSTEMS AND METHODS FOR DETERMINING INTRAOPERATIVE SPINAL ORIENTATION" and filed on Jul. 4, 2016, which is incorporated herein by reference in its entirety.

Having generated both the first and second registration transforms, these region-specific registration transforms can be dynamically employed during a navigated surgical procedure. As shown at step 220 in FIG. 2A, navigation images are intraoperatively generated and displayed by selectively employing one of the region-specific registration transforms to register the pre-operative volumetric image data to an intraoperative frame of reference.

In some example implementations of the present disclosure, it may be desirable to intraoperatively update the calculation of the registration transforms, in order to compensate for intraoperative relative changes in the position and/or orientation of the multiple surface regions (e.g. multiple anatomical bodies with independent degrees of freedom). This repeated updating of the multiple registration transforms may be particularly beneficial in applications involving the navigation of surgical procedures involving multiple rigid body elements having independent degrees of freedom, where the repeated updating of the multiple registration transforms accounts (compensates) for relative motion between the multiple rigid body elements during the procedure. The continuous updating of the multiple registration transforms may be performed by repeatedly acquiring additional surface data (e.g. structured light images) and re-registering each surface region (e.g. corresponding to a different rigid body element) independently.

In some example embodiments, the updating of the registration transforms may be automated to occur at a pre-selected time points that may or may not be periodic. For example, the updating of the registration transforms may occur at periodic time intervals. The intervals may be selected to be short enough such that the updating is perceived to be continuous. For example, the update interval may be less than 60 seconds, less than 40 seconds, less than 30 seconds, less than 20 seconds, less than 10 seconds, less than 5 seconds, less than 2 seconds, or less than one second. The time interval between updating the registration transforms may depend on the computing resources available for performing registration. In one example implementation, the time interval between updating the registration transforms may be equal to the time interval required for computing registration plus a time delay margin (where the time delay margin may be a fraction of the time interval required for computing registration).

The updating of the registration transforms is achieved by repeating, one or more times during the medical procedure, the surface detection step shown in step 205 of FIG. 2A, and subsequently re-calculating the registration transforms in step 215, and updating the display of the navigation images (using the selected registration transform) in step 220. In cases in which only the pre-operative surface data is segmented within the first and second surface regions, this segmentation step need not be repeated. However, if the method is performed according to an implementation in which only the intraoperative surface data is segmented in step 210, then the segmentation step is performed each time that new intraoperative surface data is acquired.

In one example implementation, the updating of the registration transforms can be performed automatically (e.g. in the absence of user intervention or user input, such as in the absence of user input specifying updated fiducial points), where the previous registration transforms are employed to respectively act as initial estimates for the calculation of the updated registration transforms. For example, automatic re-registration implementation may be performed if the motion between any two time points is sufficiently small that a registration quality measure (computed using the previous registration transform to register the pre-operative surface data with the newly acquired intraoperative surface data)

satisfies a criterion. In the event that the registration quality measure fails to satisfy the criterion (such as exceeding a registration error metric), the system can prompt the operator to provide new fiducial locations to support the re-registration process.

One example measure of registration quality is a registration error, which describes the mean distance between points of the pre-operative surface data to the intraoperative surface data, upon registration using the previously computed registration transform. Another example measure of registration quality is the standard deviation of the distances between points of the pre-operative surface data and the intraoperative surface data. Yet another example measure of registration quality is the number of points that are matched between the surface data. These metrics, or other suitable registration quality measures, can be used alone or in combination. One example method to combine these metrics is to evaluate the ratio of the different metrics. If two metrics disagree, the choice for a more desired registration quality can be based on the one metric whose relative difference is greatest.

The selection, from the multiple region-specific registration transforms, of a registration transform for use in transforming the volumetric image data into the intraoperative frame of reference of the tracking system for the generation of navigation images, may be made according to a wide variety of implementations, with several illustrative yet non-limiting implementations described below.

In one example embodiment, the selection of a given region-specific registration transform for the generation of navigation images, at a given point in time during the navigated procedure, is based on proximity of a tracked tool relative to each surface region. For example, for each surface region having an associated region-specific registration transform, a respective proximity measure may be calculated based, where the proximity measure is based on a computed distance between a location associated with a tracked tool and a location associated with the surface region, and where the registration measure associated with the smallest proximity measure is dynamically employed to generate navigation images based on the pre-operative volumetric image data.

For example, in the case of a spinal surgical procedure involving two spinal levels and a tracked awl, the proximity measure may be associated with a tracked location of the awl tip. The navigation images may be dynamically generated (i) using the registration transform associated with the first spinal level when the awl tip is proximal to the first spinal level (closer to a first location associated with the first spinal level than to a second location associated with the second spinal level), and (ii) using the registration transform associated with the second spinal level when the awl tip is proximal to the second spinal level (closer to a second location associated with the second spinal level than to a first location associated with the first spinal level).

The location associated with the tracked tool may be a location such as, but not limited to, a location of a tool tip, or a location of a functional portion of the tool, or a location of a center of mass of the tool. The location associated with the surface region may be a location such as, but not limited to, a geometrical center of the segmented surface region, a location of a fiducial point within the region of interest, a location associated with a tracked reference frame secured within or adjacent to the surface region, and a location proximal to the surface region by residing outside of the surface region. In some example embodiments, the proximity measure may be computed based on the locations of multiple instruments. For example, an average location may be computed based on tracked locations of multiple instruments. The average may optionally be computed using instrument-specific weighting factors.

In an alternative example embodiment, the gaze direction of a surgeon may be tracked, and the proximity measure may be associated with the gaze direction. For example, an intersection location of the intersection of the gaze direction with the patient anatomy may be computed, and the proximity measure may be determined based on the distance between the intersection location and locations associated with the first and second surface regions.

In another example embodiment, the dynamic selection of a suitable registration transform for use when generating navigation images may be determined according to user input. For example, a user input device, such as a foot pedal, keyboard, mouse, touch screens, external gesture control devices such as the Myo armband, Kinect or by internally integrating gesture control algorithms into the navigational camera systems (tracking or visible camera(s)) may be employed to facilitate the intraoperative selection of a suitable registration transform.

Figure 4A:
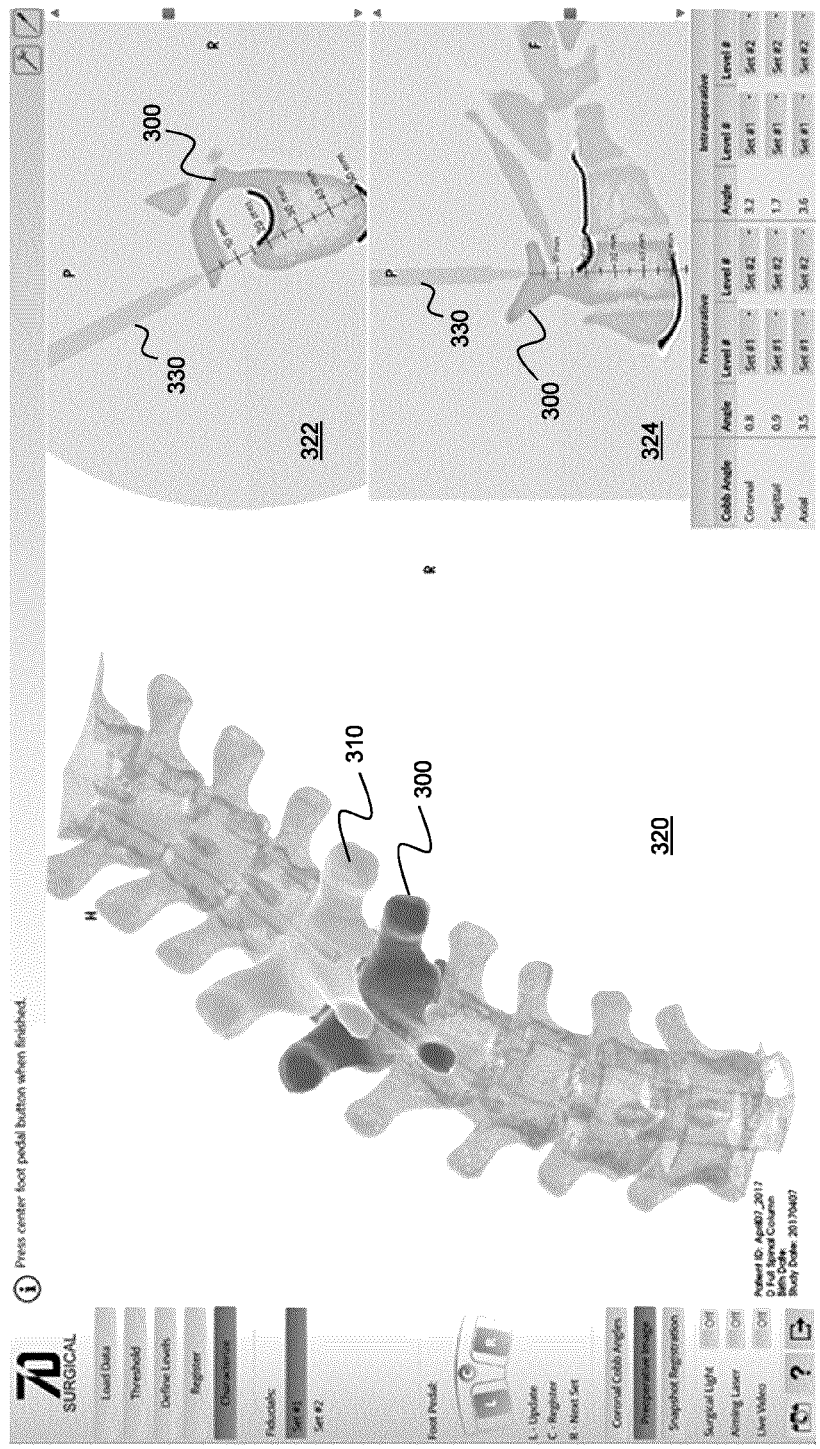
FIGS. 4A and 4B illustrate an example of a navigation user interface for performing intraoperative navigation during a spinal surgical procedure in which tool proximity is employed to dynamically select between registration transforms associated with two different spinal levels.
Figure 4B:
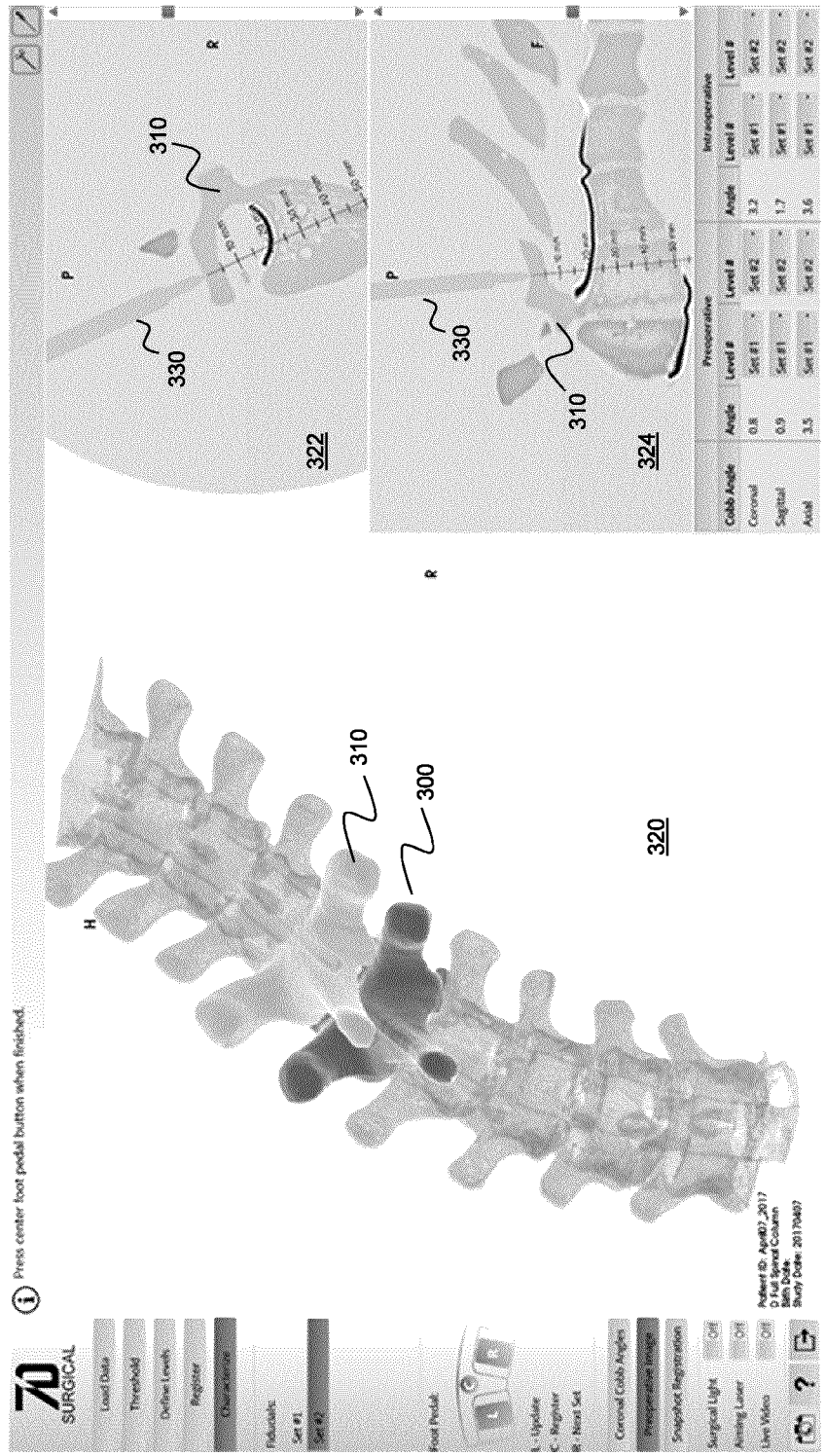

FIGS. 4A and 4B illustrate an example of a navigation user interface for performing intraoperative navigation during a spinal surgical procedure in which tool proximity is employed to dynamically select between registration transforms associated with two different spinal levels. The left window 320 of the example user interface of FIGS. 4A and 4B shows an image of the spine that is generated based on the pre-operative image data. This image is annotated to highlight, in different greyscale levels, two spinal levels (300 and 310) that are relevant to the spinal surgical procedure.

As shown in FIG. 4A, when the tracked surgical tool 330 is proximal to the first spinal level 300 (e.g. closer to the center of the first spinal level than to the center of the second spinal level, or an alternative measure of proximity), the right two windows 322 and 324 display axial and sagittal views (coronal view not shown here but it may be) of the spinal column in which the surgical tool 330 is shown spatially registered to the first spinal level 300 using the first registration transform. The cross-sectional image data of the first spinal level is obtained by applying the first registration transform (associated with the first spinal level 300) to the pre-operative volumetric image data, and computing the relevant slice through this image data. However, as shown in FIG. 4B, when the tracked tool is proximal to the second spinal level 310, the right windows 322 and 324 dynamically change to display navigation images in which the surgical tool 330 is shown spatially registered to the second spinal level 310 using the second registration transform.

Figure 2B:
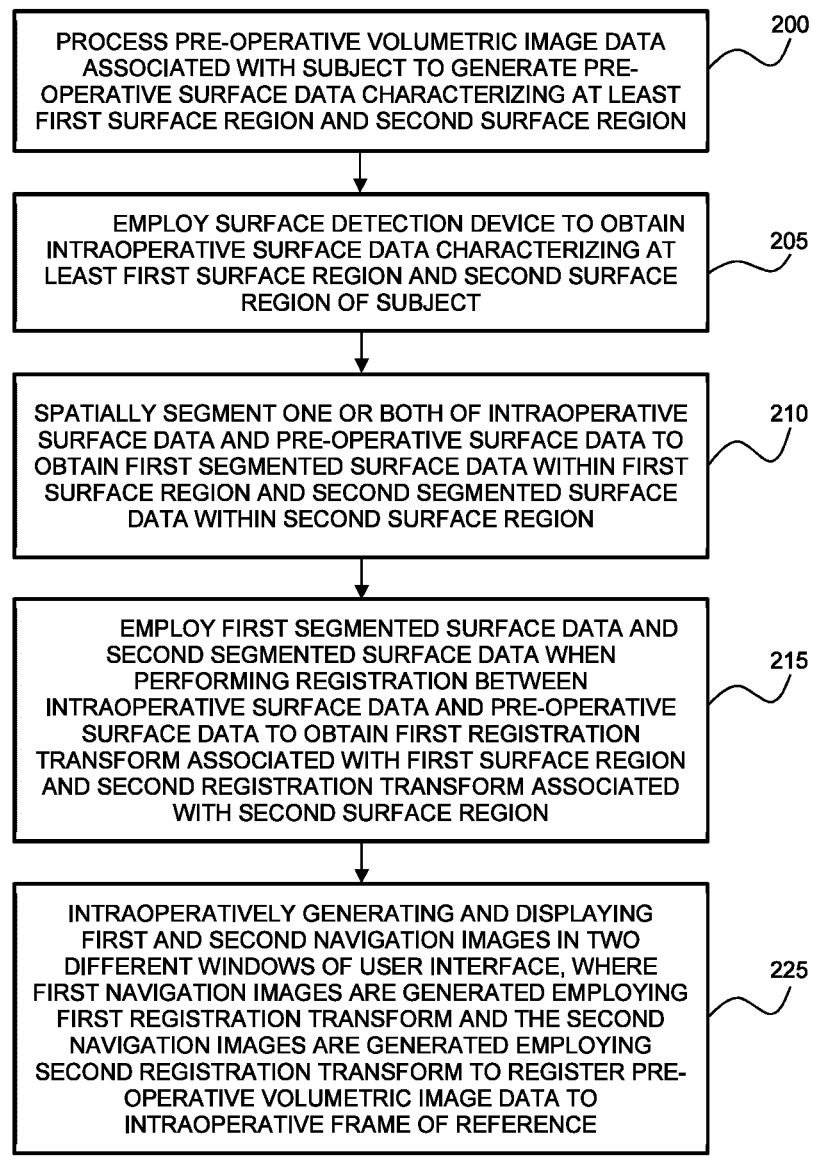
FIG. 2B is a flow chart illustrating an example method for generating surface-based navigation images for image-guided navigation of a medical procedure based on the calculation of multiple registration transforms associated with different surface regions, and the intraoperative display of navigation images based on multiple registration transforms.
Figure 4C:
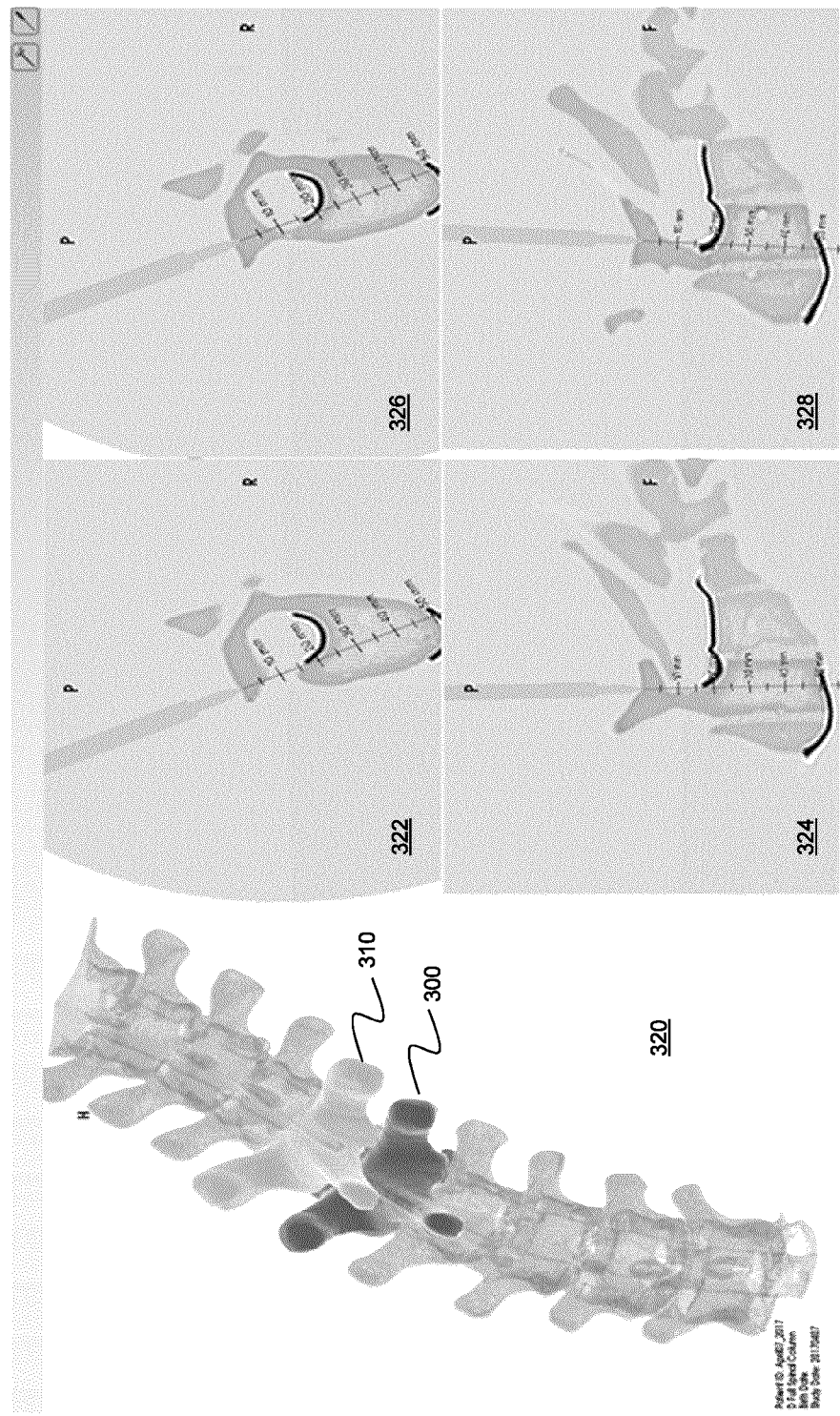
FIG. 4C displays an alternative example implementation of a navigation user interface in which navigation images are generated using both registration transforms and displayed at the same time in separate windows of the user interface.

FIG. 4C displays an alternative example implementation in which navigation images are generated using both registration transforms and displayed at the same time in separate windows of the user interface. The user interface windows 322 and 324 show cross-sectional navigation images based on the first registration transform, while the user interface windows 326 and 328 show cross-sectional navigation images based on the second registration transform. Such an example embodiment need not employ the dynamic selection of a single registration transform, since both windows are displayed at the same time and separately employ the respective registration transforms of the first and second surface regions. This example embodiment is further illustrated in the flow chart shown in FIG. 2B, in which step 225 involves the displaying of first and second navigation images generated with the respective first and second registration transforms.

Although many of the example embodiments provided herein refer to first and second surface regions of patient anatomy for performing separate intraoperative registration, it will be understood that the present disclosure is not intended to be limited to the intraoperative registration of two surface regions. The various example embodiments and implementations described herein may be extended to three or more surface regions (e.g. three or more rigid bodies that have independent degrees of freedom).

Figure 5A:
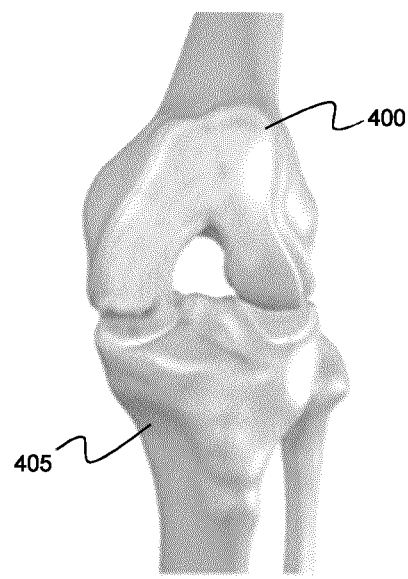
FIGS. 5A and 5B show the shoulder joint and the knee joint, respectively, providing examples of anatomical bodies having multiple surface regions that are separated by a joint, and thus one or more independent degrees of freedom.
Figure 5B:
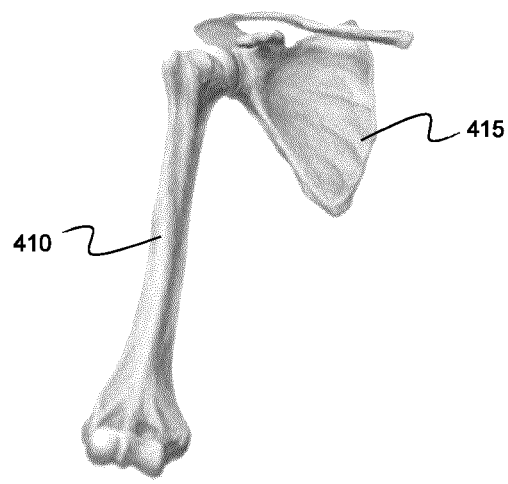

Many of the example embodiments described in the preceding disclosure are illustrated in the context of spinal procedures. However, it will be understood that the example embodiments of the present disclosure may be adapted and applied to a wide variety of surgical procedures. In some example implementations, the example embodiments of the present disclosure may be employed to perform intraoperative registration to multiple surface regions for surgical procedures involving anatomical bodies that are separated by a joint, and thus have one or more independent degrees of freedom. One example of such a surgical procedure is a procedure performed on the knee joint, which is shown in FIG. 5A. For example, the navigation of partial and total knee replacement procedures could be improved by independently registering and tracking both the femur 400 and the tibia 405, thereby obtaining separate registration transforms associated with each bone. The separate and independent registration transforms could be employed for the intraoperative dynamic selection of a suitable registration transform, according the example embodiments provided above, thereby facilitating improved placement of implants. FIG. 5B illustrates the application of the present example embodiments to surgical procedure involving the shoulder joint, in which both separate registration transforms would be obtained for both the humerus 410 and the scapula 415.

Figure 6A:
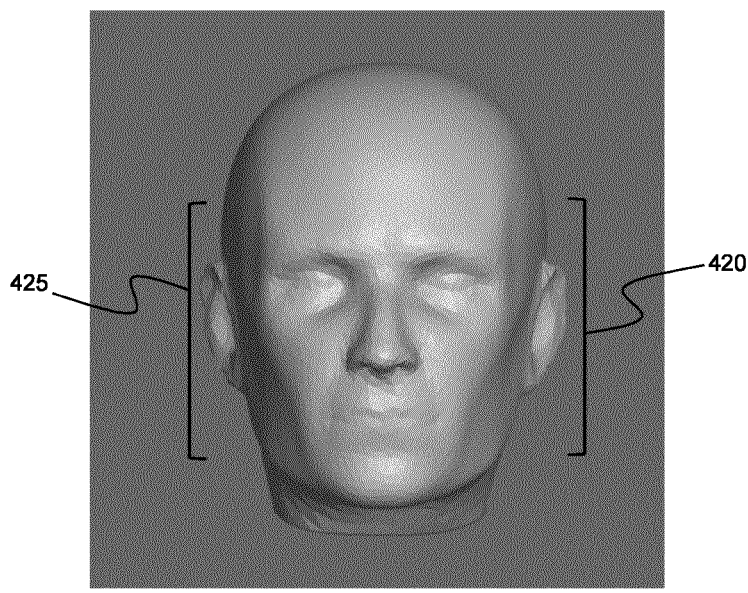
FIGS. 6A and 6B show different surface regions of the cranium are not separated by a joint.
Figure 6B:
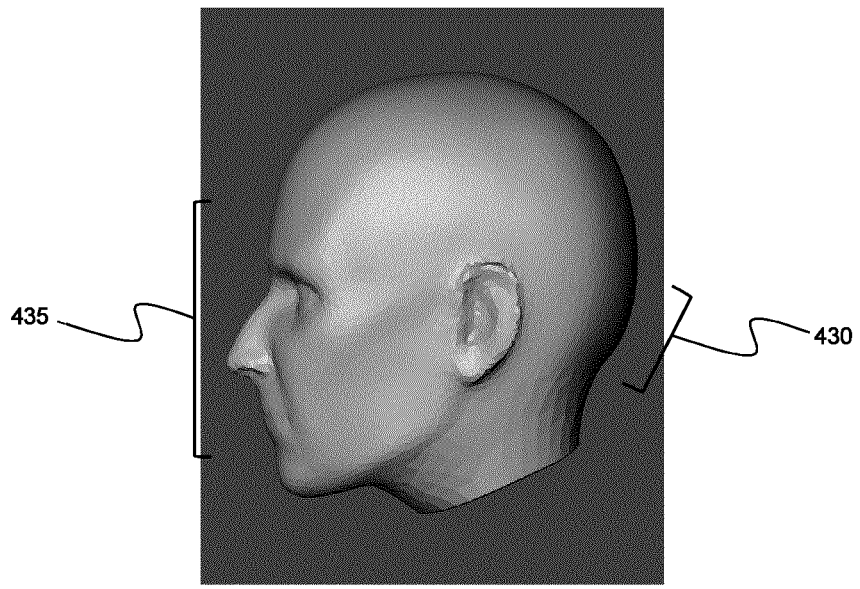

In some example embodiments, the two or more surface regions for which registration transforms are independently obtained need not be separated by a joint. FIGS. 6A and 6B illustrate an example implementation of such an embodiment, as applied to a surgical procedure involving the cranium. The figures show different example surface regions for performing separate and independent intraoperative registration. These example surface regions include different regions of the head, such as the left 420 and right 425 sides of the head, and different regions of the skull such as the posterior fossa 430 and anterior (facial) 435 regions. The independent registration to two or more different regions of the cranial anatomy can be beneficially applied to cranial surgical procedures that involve different regions at different times.

Indeed, for many cranial surgeries, navigation is used during two distinct spans in time, such as during an initial non-sterile phase and later during a sterile phase. Non-sterile usage occurs before the surgeon has "scrubbed in" and allows the surgeon to plan where the entry point will be and the size of the skin flap/incision required. The registration during non-sterile usage is currently performed using the face. In cases in which the planned surgical entry point at the back of the head, a second registration would need to be performed on the bony surface at the back of the head during the sterile part of the procedure. When this new registration transform becomes available, the system can dynamically switch to this registration transform from a previously acquired registration transform obtained based on the facial region, as per the example methods described above, such that the second registration transform is subsequently employed when the procedure is conducted in the vicinity of the back of the head (e.g. via proximity-based registration transform switching as described above). If the situation arises that navigation at the front of the face is required, the registration transform obtained by previously registering the front of the face can be recalled, without the need to perform a new registration. This can be especially useful in scenarios where the front of the face may no longer be available for registration, for example, when the face is covered by drapes.

In the more general case, in which a surgical target is deeply situated (e.g. in or near the center of the head) it may be beneficial to acquire, for the non-sterile phase, multiple registration transforms based on multiple surface regions, to enable the selective use of suitable registration transform (e.g. left and right sides of the head). In such a navigated procedure, the surgeon would have a number of different options with regard to how to access the target anatomy, and maintaining the highest degree of accuracy in each surface region as the entry point is planned would be beneficial.

Figure 7A:
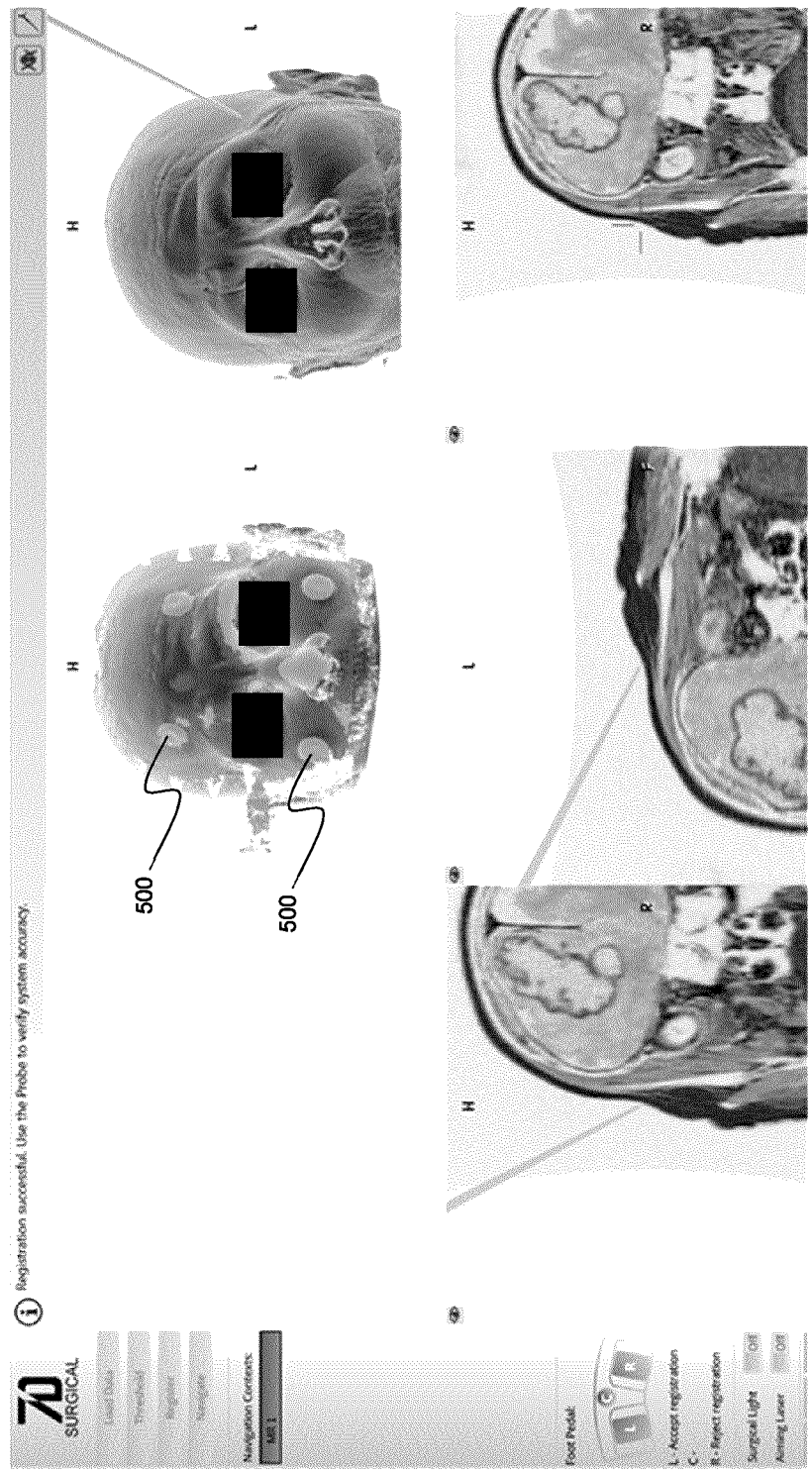
FIG. 7A and FIG. 7B show an example user interface that is configured to dynamically display navigation images based on the dynamic selection of a registration transform from two different registration transforms that are separately computed based on an anterior surface region and a posterior surface region (the posterior fossa surface region).
Figure 7B:
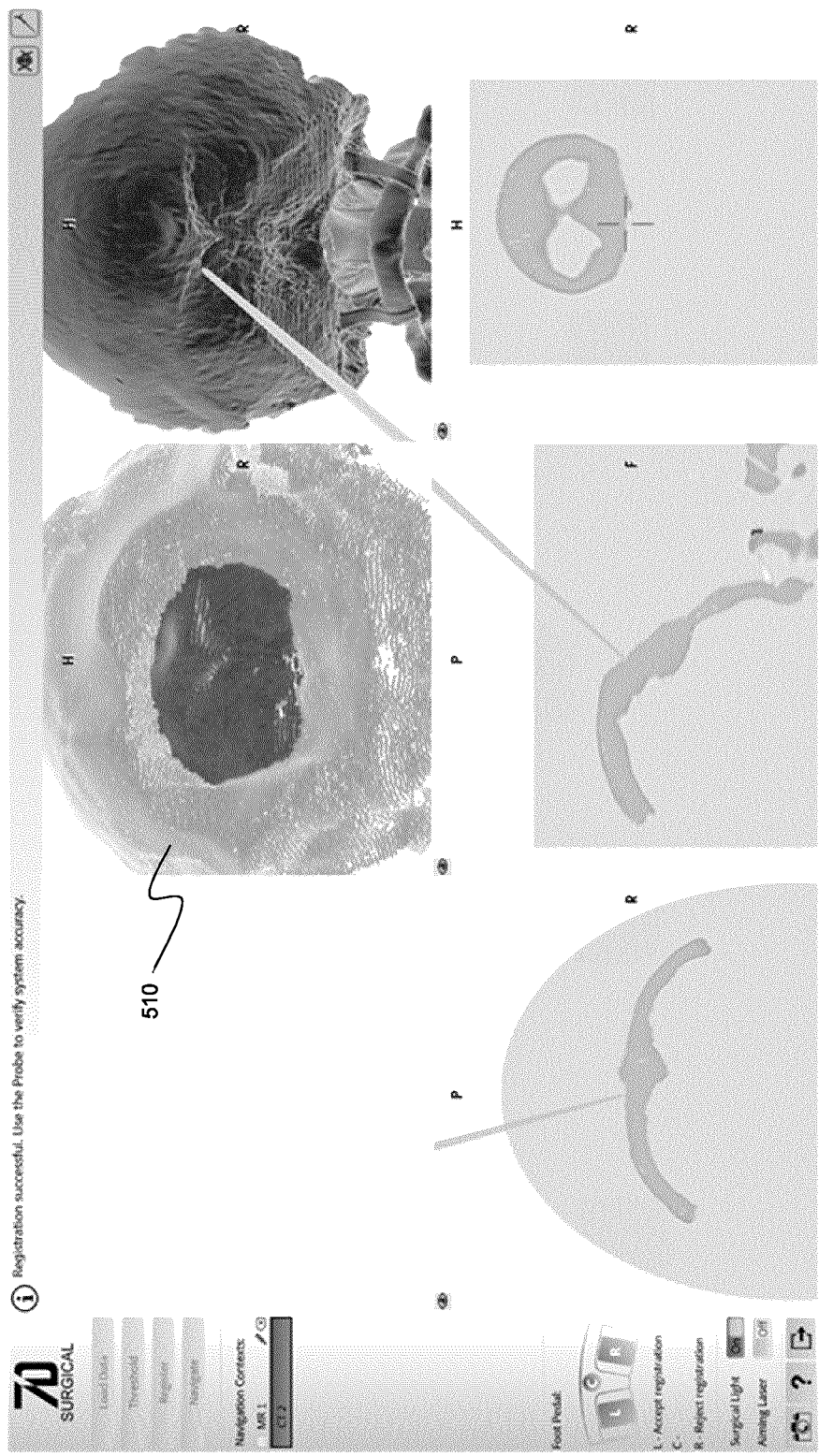

FIGS. 7A and 7B show an example user interface that is configured to dynamically display navigation images based on the dynamic selection of a registration transform from two different registration transforms that are separately computed based on an anterior surface region and a posterior surface region (the posterior fossa surface region). In FIG. 7A, an MRI dataset is used to generate the preoperative surface data for registration to the anterior surface of the patient (face) at the beginning of the procedure. FIG. 7B shows a time point later in the procedure after the tissue has been resected from the bone in the posterior fossa region and a CT scan was used to generate a second pre-operative surface data of the bone. The top middle panels of FIGS. 7A and 7B show the segmentation of the intraoperative surface data used to generate each of the registration transforms. The light grey regions 500 in FIG. 7A (also present on the right side of the face, the nose and above the right eye socket) and the light gray region 510 in FIG. 7B represent regions that were rejected and not used during registration. The top right panel is the 3D model of the pre-operative datasets superimposed with the tracked tool. The bottom three panels show the axial, sagittal and coronal navigational views also superimposed with the tracked tool.

Referring again to the example embodiment illustrated in the flow chart shown in FIG. 2A, the intraoperative registration performed in step 215 may be performed based on an initial registration that employs per-region volumetric fiducial points and corresponding per-region intraoperative fiducial points. In one example embodiment, the volumetric fiducial points are obtained based on input from a user or operator. For example, a user may employ a user interface to select, on a display showing the pre-operative surface data, at least three volumetric fiducial points for each surface region (e.g. each anatomical body having independent degrees of freedom). As noted above, surface segmentation of the pre-operative surface data to obtain segmented pre-operative surface data for a given surface region may be performed using at least one volumetric fiducial point from the given surface region to initialize a region growing surface segmentation method.

The per-region intraoperative fiducial points may also be obtained based on input from a user or operator. In one example implementation, a user may employ a tracked probe (e.g. a probe having fiducial markers attached thereto that are tracked with a tracking system) to select, via contact with different locations on exposed anatomy, intraoperative fiducial points for each surface region, where the intraoperative fiducial points correspond to the volumetric fiducial points on a per-region basis. In such a case, a tracked reference frame attached to the subject (e.g. reference frame 55 shown in FIG. 1) may be employed to compensate for the motion of the spine during point selection.

In some example embodiments, one or more of the intraoperative and preoperative fiducial points may be generated automatically using image processing methods to detect anatomical features and/or landmarks. In one example implementation, intraoperative fiducial points are generated using facial recognition to locate the position of the facial landmarks such as the eyes and nose the intraoperative surface image data. Image processing methods for the automated identification of anatomical features and/or landmarks. For example, the following algorithms may be employed for the identification of facial features and/or landmarks: Google's face detection API (https://www.sitepoint.com/face-detection-in-android-with-google-play-services/); face and eye detection using Haar Feature-based Cascade Classifiers (http://docs.opencv.org/trunk/d7/d8b/tutorial_py_face_detection.html); and the highly cited facial recognition system pioneered by Viola and Jones (viola01rapid.pdf) for recognizing the face, and subsequently different parts of the recognized faced, such as the eyes and the nose.

The two-dimensional image points corresponding to the detected anatomical features can then be re-projected into three-dimensional space using well-known camera calibration routines based on extrinsic and intrinsic parameters (e.g. focal, principal point, skew, distortion coefficients), for example, as described by Bradski et al. [G. Bradski and A. Kaehler, "Learning OpenCV", 2008].

Similarly, one or more of the pre-operative volumetric fiducial points can be automatically generated from the pre-operative volumetric image data. For example, the pre-operative volumetric image data can be processed using facial recognition methods on a two-dimensional image of the rendered volume. The detected two-dimensional image points can then be re-projected into three-dimensions using the render window camera parameters, as described above.

In some example implementations, one or both the pre-operative surface data and the intraoperative surface data may be processed for the direct three-dimensional generation of fiducial points. This may be achieved, for example, using a model-based algorithm, in which a mathematical model of the patient anatomy is fitted or deformed to the surface data. In one example, a mathematical model of the cranial anatomy may include labels corresponding to the eye and/or nose (e.g. Collins_et_al-1995-Human_Brain_Mapping.pdf). In one example implementation, if three or more of the same features are detected in both pre-operative surface data and the intraoperative surface data, then the detected features can be employed as fiducial points when performing an initial landmark-based registration prior to surface-to-surface registration.

Figure 8A:
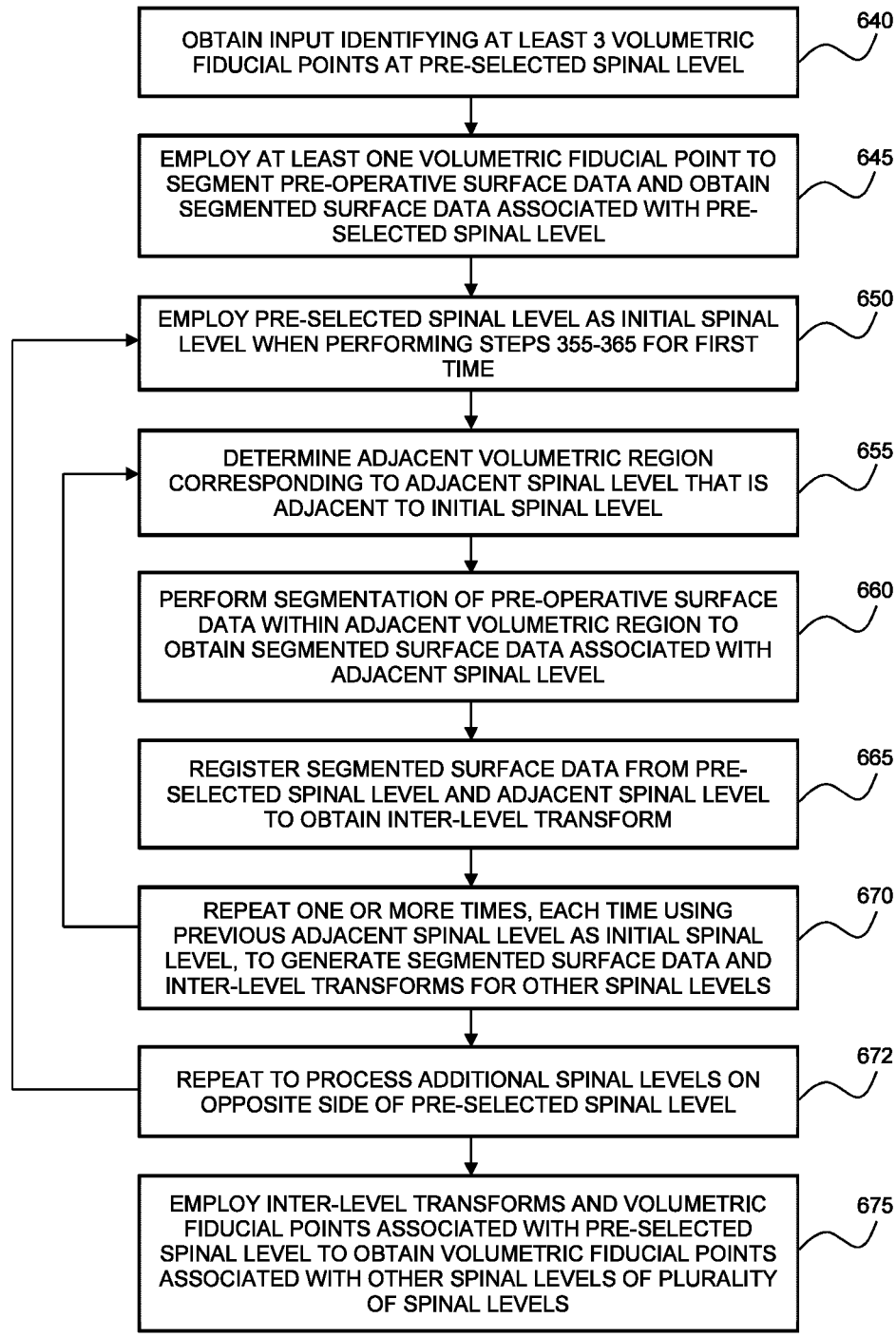
FIG. 8A is a flow chart illustrating an example method of generating segmented surface data and volumetric fiducial points for a set of spinal levels in the volumetric frame of reference, based on volumetric fiducial points identified at a pre-selected spinal level.

In one example embodiment, volumetric fiducial points are obtained for a pre-selected surface region (e.g., a pre-selected anatomical body that moves with independent degrees of freedom relative to another anatomical body), based on input from a user or operator, and the remaining volumetric fiducial points (and the segmented surface data) are automatically generated for the other surface regions. An example of a method, illustrated within the context of a spinal surgical procedure involving multiple spinal levels, is illustrated in FIG. 8A. It will be understood that the example method described below may be applied to other anatomical regions that involve multiple bodies connected through a joint.

Figure 9A:
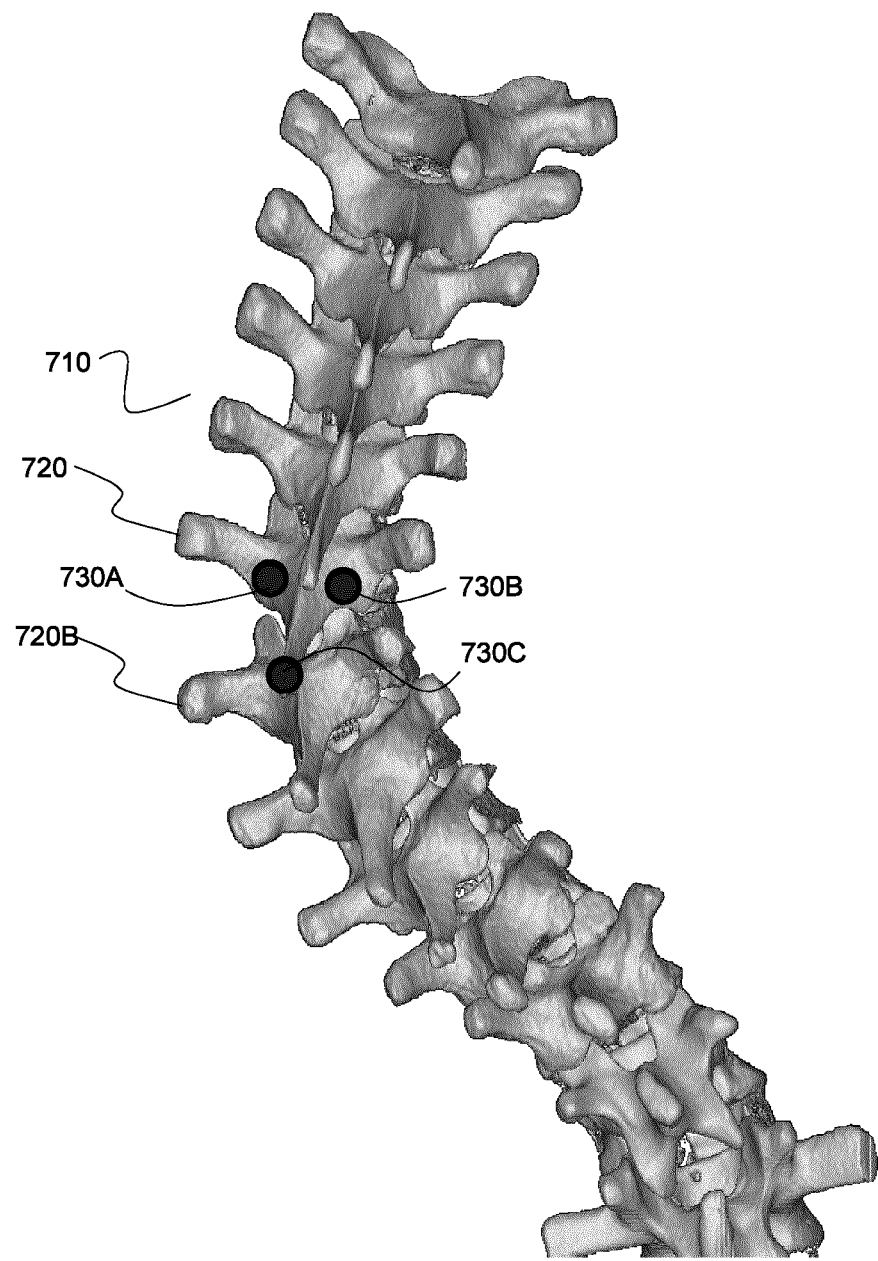
FIG. 9A illustrates an example multi-level surface generated by thresholding volumetric image data of the spine to determine a surface corresponding to bone, showing the pre-selected spinal level that is expected to correspond to a selected intraoperatively exposed spinal level. The figure also shows three volumetric fiducial points located at the pre-selected spinal level.

As shown at step 640 of FIG. 8A, input is received from a user identifying, in the pre-operative surface data, at least three volumetric fiducial points associated with a pre-selected spinal level that is expected to be exposed during the surgical procedure. For example, as shown in FIG. 9A, the pre-operative surface 710 is employed for the selection of a set of at least three volumetric fiducial points, shown at 730A-C, at the pre-selected spinal level 720. The volumetric fiducial points 730A-C, which may be selected by an operator on a user interface displaying the pre-operative surface data 710, identify the pre-selected spinal level 720 that is expected to be exposed during a surgical procedure.

Figure 9B:
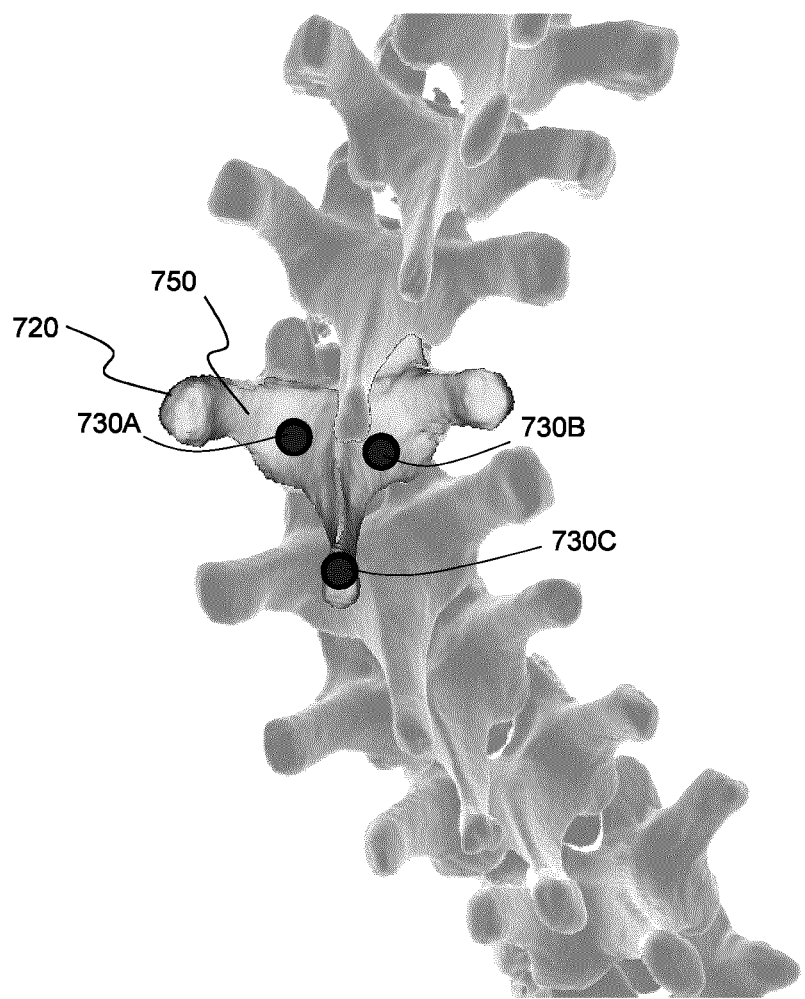
FIG. 9B illustrates an example segmented surface, obtained by segmenting the multi-level surface of FIG. 9A at the pre-selected spinal level (as identified by the volumetric fiducial points).

Having identified the volumetric fiducial points 730A-C, the pre-operative surface data 710 may be processed to generate the segmented surface data associated with the pre-selected level 720, as shown at step 645 in FIG. 8A. An example of the segmented surface data 750 is shown in FIG. 9B, which also shows the volumetric fiducial points 730A-C. The segmented surface data 750 includes surface data corresponding to the pre-selected level 720. Segmentation of the pre-operative surface data to obtain the segmented surface data may be performed according to any suitable method (such as those described above). One or more of the volumetric fiducial points may be employed to initiate surface segmentation.

Having performed surface segmentation of the pre-selected spinal level, the pre-selected spinal level, and its associated segmented surface data, is employed for the generation of segmented surface data associated with an adjacent spinal level, as shown in steps 650 to 665 of FIG. 8A. An example of an adjacent level is shown in FIG. 9A at 720B. Unlike the pre-selected spinal level 720, the adjacent spinal level 720B does not have associated volumetric fiducial points to support surface segmentation from the pre-operative surface data, or to support registration with the intraoperative surface data.

In order to facilitate surface segmentation of an adjacent spinal level, an adjacent volumetric region, such as a bounding box (the region need not be a rectangular prism) is identified in which to perform segmentation, as shown at step 655. The determination of the adjacent volumetric region may be made based on a determination of directional information associated with the orientation of the spine, where the directional information enables the determination of a direction in which to locate the adjacent spinal level. The directional information can be a direction which defines the entire spine. Alternatively, the directional information can be described by a spline or a piece-wise linear function to follow the shape of the spine.

This directional information may be obtained according to a variety of methods, non-limiting examples of which are provided below. In one example implementation, the directional information may be obtained from information associated with the volumetric image data, such a superior-inferior direction provided from the DICOM header. In another example implementation, an axis associated with the orientation of the spine may be determined from principal component analysis. In another example implementation, image processing methods may be applied to the volumetric image data to extract an estimated shape of the spine.

In one example implementation, a set of local spine axes may be determined, thereby providing directional information on a per-level basis. A preferential axis is initially determined for segmenting the volumetric image data. The preferential axis may be determined, for example, from information associated with the volumetric image data, such a superior-inferior direction provided from a DICOM header, or from principle component analysis. The preferential axis may then be employed to segment the volumetric image data into a series of volumetric slabs that are arranged along the preferential axis, each of which are analyzed to locate the spine. The choice of slab thickness depends on the resolution required for computing the directional information of the spine. On the other hand, if the slab thickness is too thin, the accuracy of the finding the spine within the slab, and hence deriving the directional information, may be degraded, due to reduction of signal (e.g. structured belong to the spine) to noise (e.g. the background). A slab thickness of approximately half of the length of a spinal level is typically suitable.

Various methods can be employed to analyze the slabs in order to derive the directional information of the spine. One example method can be template-based, wherein the slabs are compared to a pre-computed atlas of different vertebra. Alternatively, a user-defined threshold can be used to define a contour and/or isosurface of the bone, from which the vertebra region within the slab can be identified. The vertebra region can be identified by performing an iterative search for structures that resemble the vertebra according to a pre-computed atlas. Alternatively, an atlas-free method can be employed, which utilizes one or more volumetric fiducial points as a starting point via an iterative search.

For the atlas-free method, an initial volumetric slab segment containing one or more of the volumetric fiducial points is identified. An initial bounding box (or other suitable confining volumetric region) is then determined, where the initial bounding box contains, and is centered on, or approximately centered on, one or more of the fiducial points. The size of the initial bounding box may be determined, for example, based on the spatial extent of the segmented surface data associated with the pre-selected spinal level, or based on an estimated spatial extent of an average spinal level. This initial volumetric slab segment is processed, within the initial bounding box, to determine an initial center of mass of bony structures within the initial volumetric slab segment. This process may be repeated one or more times, where each time, the bounding box is re-centered on the most recently identified center of mass location. The center of mass location may be iteratively refined in this manner until a pre-selected convergence criterion has been met, such as the change in the center of mass location between subsequent iterations is below a threshold.

Once the center of mass corresponding to the spine has been determined in the initial volumetric slab, an adjacent bounding box may then be determined, within an adjacent slab. Since the bounds of a vertebra is approximately the same within the same patient, the adjacent bounding box can be of the same size as the bounding box from the initial volumetric slab, wherein the center of the adjacent bounding box can be initialized with the center of mass from the initial volumetric slab. This adjacent volumetric slab segment is processed similarly, within the adjacent bounding box, to determine an adjacent center of mass location within the adjacent volumetric slab segment. As noted above, this process may be repeated one or more times, where each time, the bounding box is re-centered on the most recently identified center of mass location, iteratively refining the center of mass location until a pre-selected convergence criterion has been met.

The above method of finding an adjacent center of mass location in an adjacent volumetric slab segment may then be repeated one or more times in order to determine center of mass locations within a plurality of the volumetric slab segments, thereby allowing the determination of a local axis, based on two or more center of mass locations. In one example implementation, the local axis associated with two neighboring volumetric slab segments may be employed to locate the bounding box within an adjacent volumetric slab region when performing the aforementioned method.

In situations where the initial preferential axis is significantly different than the directional information of the spine (e.g. due to disease), the computed directional information can be used to again segment the volumetric image data into a series of volumetric slabs, and the above iterative center finding method repeated to refine the directional information of the spine.

After obtaining the directional information (e.g. global or local), this information may be employed to determine an adjacent volumetric region within which to perform segmentation of the pre-operative surface data in order to obtain the adjacent segmented surface data corresponding to the adjacent spinal level, as per step 655 of FIG. 8A. For example, an adjacent bounding box for segmenting the adjacent spinal level may be centered at a location, relative to one or more of the volumetric fiducial points, which lies along an axis obtained based on the directional information, such that the bounding box is expected to contain the adjacent spinal level. The spatial separation between the center of the adjacent bounding box and the one or more volumetric fiducial points may be determined, for example, based on the spatial extent of the segmented surface data associated with the pre-selected spinal level, or based on reference anatomical data (e.g. atlas data) characterizing an estimated spatial separation between the pre-selected spinal level and the adjacent spinal level.

The pre-operative surface data may then be processed within the adjacent bounding box to generate the segmented surface data associated with the adjacent spinal level, as shown at step 660. As noted above, the segmentation of the pre-operative surface data to obtain the adjacent segmented surface data may be performed according to any suitable method.

An inter-level transform is then determined between the pre-selected spinal level and the adjacent spinal level, as shown at step 665. The inter-level transform between the pre-selected spinal level and the adjacent spinal level may be determined by performing registration between the segmented surface data (associated with the pre-selected spinal level) and the adjacent segmented surface data (associated with the adjacent spinal level). The inter-level transform between the segmented surface data of the pre-selected spinal level and the adjacent segmented surface data is defined by following the pre-computed directional information, translating by a distance that is based on the spatial extent of the segmented surface data, or using reference anatomical data (e.g. atlas data) characterizing an estimated spatial separation between the initial spinal level and the adjacent spinal level. Fine-tuning of the registration is then performed by any suitable registration algorithm. It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

Having obtained the inter-level transform between segmented surface data of the pre-selected spinal level and the adjacent segmented surface data, the position and orientation of the adjacent spinal level, relative to that of the pre-selected spinal level, is known. This process of determining the segmented surface data for an adjacent spinal level, and an inter-level transform from the initial spinal level to the adjacent spinal level, may then be repeated for additional adjacent spinal levels, as shown at step 670. As per step 650, when steps 655-665 are performed for the first time, the pre-selected spinal level is employed as an initial level for determining the segmented surface data and the inter-level transform to the adjacent spinal level. However, as per step 670, each time steps 655-665 are repeated, the previous adjacent level is employed as the initial level, such that the newly determined segmented surface data and the newly determined inter-level transform pertains to the next adjacent spinal level. This process is repeated if other spinal levels, of the plurality of spinal levels that are intraoperative exposed, reside on the opposing side of the pre-selected spinal level, as shown at step 672.

After having performed steps 640 to 672, segmented surface data is obtained for each spinal level, and inter-level transforms are obtained between each set of adjacent spinal levels, based on the volumetric fiducial points provided for the pre-selected spinal level. As shown at step 675, the inter-level transforms may be applied to volumetric fiducial points in order to generate, on a per-level basis, volumetric fiducial points associated with the additional spinal levels. The volumetric fiducial points and segmented pre-operative surface data may therefore be obtained for multiple surface regions (e.g. a first surface region and a second region, which need not be adjacent to one another).

Figure 10A:
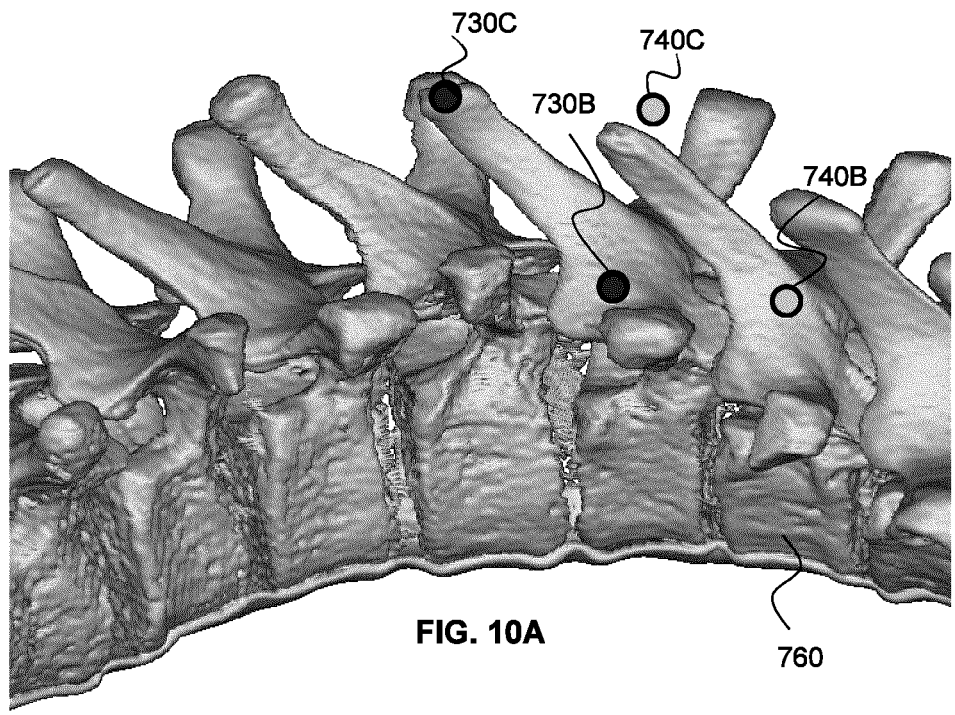
FIG. 10A illustrates the process of shifting the volumetric fiducial points via the inter-level transform, in order to generate adjacent volumetric fiducial points at an adjacent spinal location.

As a first step, the inter-level transform between the pre-selected spinal level and the adjacent spinal level may be employed to determine locations, in the adjacent segmented surface data, of adjacent volumetric fiducial points. According to this example implementation, and as illustrated in FIG. 10A, the inter-level transform may be applied to the locations of the volumetric fiducial points 730A-C associated with the pre-selected fiducial points in the volumetric frame of reference, such that the volumetric fiducial points 730A-C are transformed to the region associated with the adjacent spinal level (FIG. 10A shows volumetric fiducial points 730B and 730C, as volumetric fiducial point 730A is hidden in the view shown).

Figure 10B:
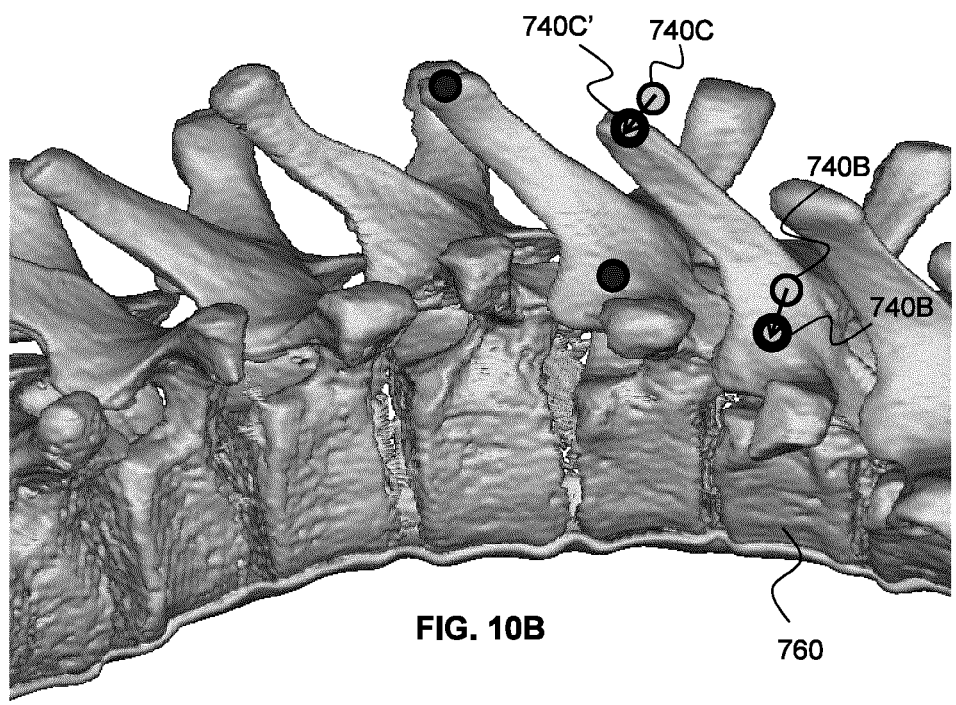
FIG. 10B demonstrates an example method of "snapping" the shifted volumetric fiducial points onto the adjacent segmented surface.

Since the segmented surface data that is associated with the pre-selected spinal level is different than the adjacent segmented surface data associated with the adjacent level, the transformed volumetric fiducial points 740A-C may not lie within the adjacent surface data. This effect is illustrated in FIG. 10B, where, for example, transformed points 740B and 740C initially lie above the adjacent segmented surface 760. In order to bring the transformed points 740A-C into the adjacent segmented surface data, the transformed points 740A-C may be shifted so that they lie within the adjacent segmented surface, as shown at points 740B' and 740C' in FIG. 10B.

For example, this may be achieved by computing a location within the adjacent segmented surface data that is nearest to the transformed point, and shifting ("snapping") the transformed point to this nearest location, thereby obtaining the adjacent volumetric fiducial point that lies within the adjacent segmented surface data. Alternatively, the point shifting procedure may be performed by computing the local surface normal vector that is directed at the transformed fiducial point, and shifting the transformed fiducial point along the direction corresponding to this vector. Optionally, in combination with these methods of shifting the fiducials, multiple candidate nearest locations on the adjacent segmented surface may be evaluated, wherein the choice is made on a similarity measure of each candidate to the fiducial on the segmented data. This similarity measure can be based on surface normals and curvatures in addition to proximity.

Figure 11A:
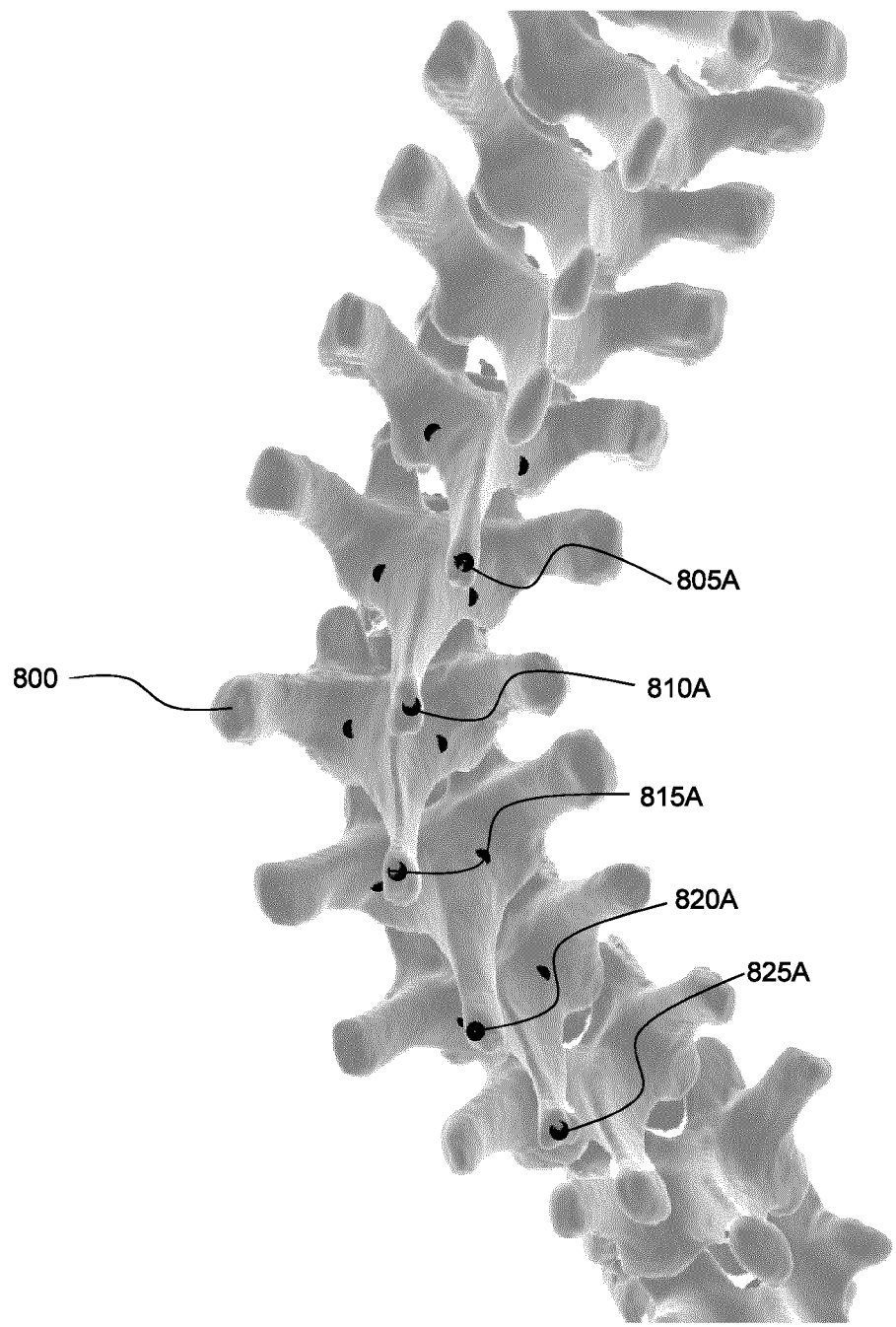
FIG. 11A illustrates the use of inter-level transforms among adjacent levels in order to generate, based on a set of selected volumetric fiducial points associated with a selected level, additional volumetric fiducial points associated with additional levels.
Figure 11B:
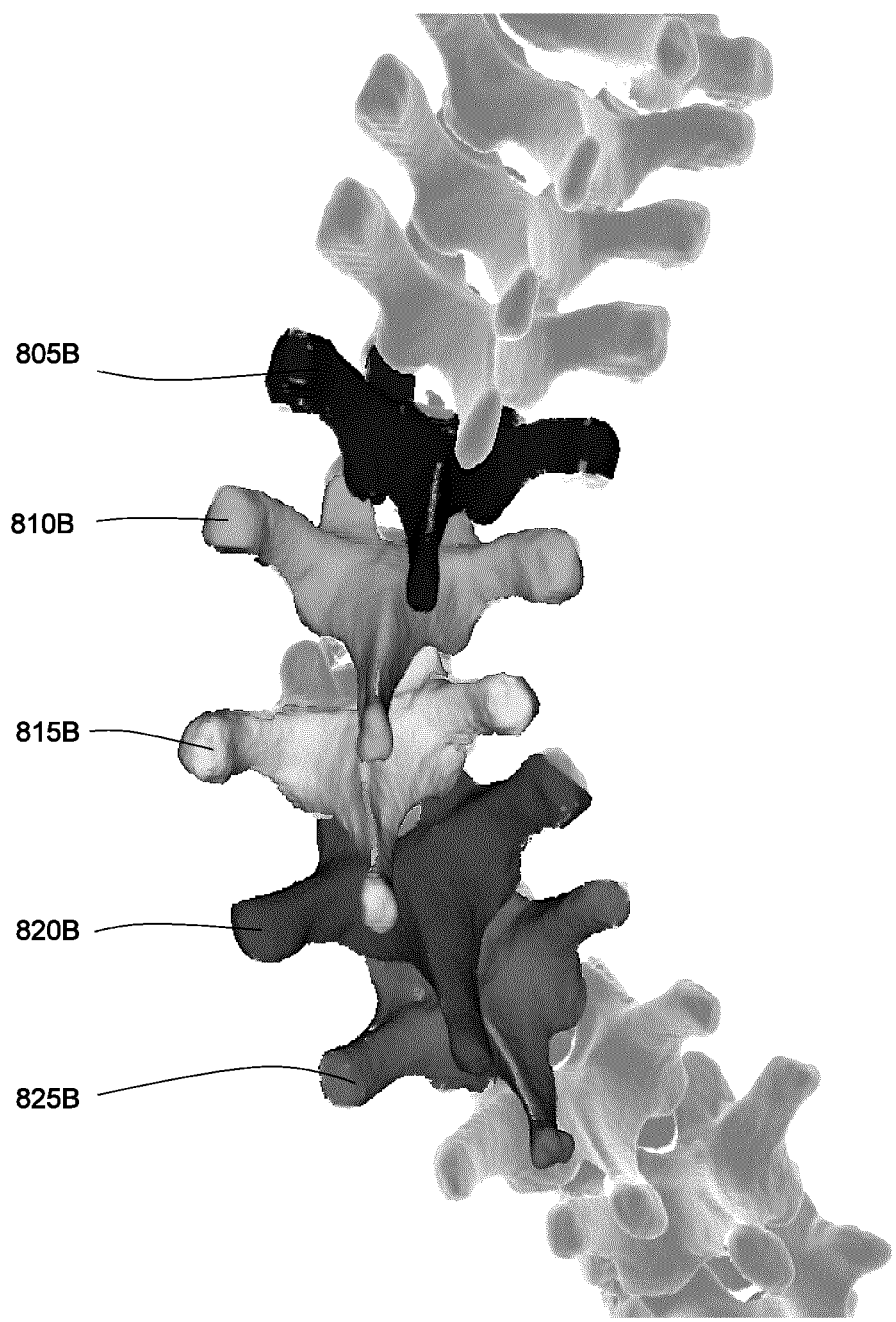
FIG. 11B illustrates a multi-level surface generated based on volumetric image data, showing the segmentation of surfaces associated with different levels to obtain per-level segmented surface data.

This process of generating adjacent volumetric fiducial points may be repeated to generate the volumetric fiducial points for the next adjacent spinal level, where the next inter-level transform is applied to the most recently determined adjacent volumetric fiducial points (e.g. after performing the aforementioned "snapping" process). This method may be repeated to generate the volumetric fiducial points for all of the relevant spinal levels, thereby generating a set of per-level volumetric fiducial points for multiple surface regions. This process is illustrated in FIGS. 11A and 11B, where user-identified volumetric fiducial point 815A associated with a pre-selected spinal level 800 is employed to generate per-level volumetric fiducial points 805A, 810A, 820A and 825A (shown in FIG. 11A) and per-level segmented surfaces 805B, 810B, 815B, 820B and 825B (shown in FIG. 11B).

As noted above, in one example embodiment, the intraoperative fiducial points for performing registration between the pre-operative surface data and the intraoperative surface data for the first spinal level and the second spinal level may be provided manually via input from a user or operator. However, in another example embodiment, the intraoperative fiducial points may be obtained for a selected level, based on input from a user or operator, and where the intraoperative fiducial points for the selected level correspond to the volumetric fiducial points defined at a corresponding level in the volumetric frame of reference. For example, FIG. 9C shows intraoperative surface data with corresponding operator-identified fiducial points. The intraoperative fiducial points are then automatically generated for the other spinal levels (thereby obtaining intraoperative fiducial points for the first spinal level and the second spinal level) in the intraoperative frame of reference. An example of such a method is illustrated in FIG. 8B.

Figure 8B:
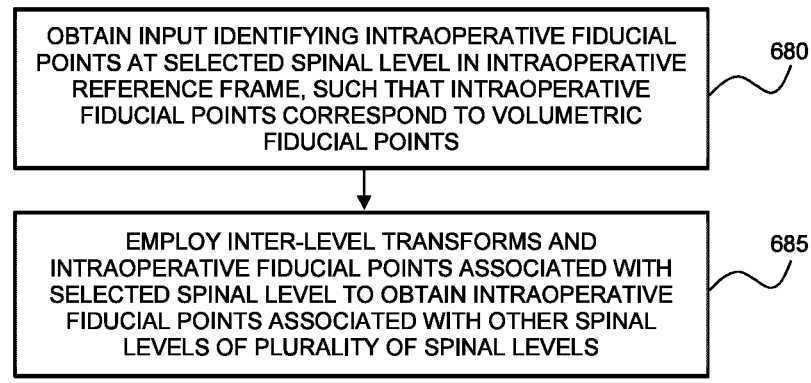
FIG. 8B is a flow chart illustrating an example method of generating intraoperative fiducial points for a set of spinal levels in the intraoperative frame of reference, based on intraoperative fiducial points identified at a selected spinal level.
Figure 9C:
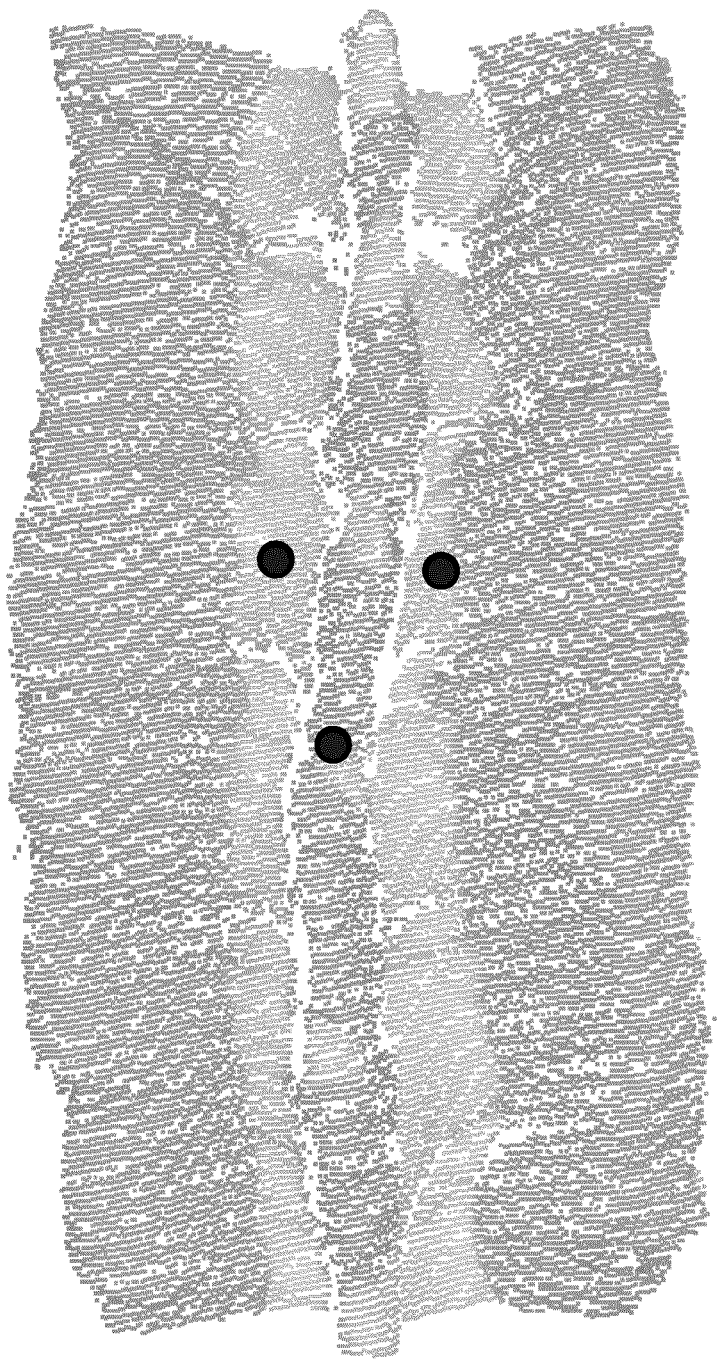
FIG. 9C illustrates an intraoperative surface detected using a surface detection system, showing several intraoperatively exposed spinal levels. Three intraoperative fiducial points, corresponding to the volumetric fiducial points, identify the intraoperatively selected spinal segment that is believed to correspond to the pre-selected spinal level in the volumetric frame of reference.

As shown at step 680 of FIG. 8B, input is received from a user identifying, volumetric fiducial points associated with a selected level in the intraoperative frame of reference. In one example implementation, a user may employ a tracked probe (e.g. a probe having fiducial markers attached thereto that are tracked with a tracking system) to select, via contact with the spine at a selected level, the intraoperative fiducial points for the selected level, where the intraoperative fiducial points correspond to the volumetric fiducial points at a corresponding level in the volumetric frame of reference.

As per step 685, the inter-level transforms, defined among pairs of adjacent spinal levels in the volumetric frame of reference (as explained above) may then be employed to generate the intraoperative fiducial points for the other spinal levels in the intraoperative frame of reference. If the volumetric fiducial points for the spinal levels were generated automatically, then these inter-level transforms will have already been computed. If the volumetric fiducial points were defined manually, then the inter-level transforms in the volumetric frame of reference may be determined by generating segmented surface data for each spinal level, using at least one of the volumetric fiducial points for each level to initiate segmentation, and then performing surface registration among adjacent levels, as per the method described above.

As a first step when generating adjacent intraoperative fiducial points, the inter-level transform between the spinal level in the volumetric frame of reference that corresponds to the selected spinal level in the intraoperative frame of reference, and the adjacent spinal level, may be employed to determine locations in the intraoperative frame of reference, of adjacent intraoperative fiducial points. This method operates under the assumption that even through the spine orientation will likely have changed in the intraoperative frame of reference relative to the spine orientation in the volumetric frame of reference, the inter-level change between adjacent levels will be sufficiently small such that the inter-level transform from the volumetric frame of reference is a valid approximation of the spatial relationship between adjacent levels in the intraoperative frame of reference.

According to this example implementation, the inter-level transform (obtained from the volumetric frame of reference) may be applied to the locations of the intraoperative fiducial points associated with the region associated with the pre-selected spinal level in the intraoperative frame of reference, such that the intraoperative fiducial points are transformed to the region associated with the adjacent spinal level, in a manner similar to the illustration in FIG. 10A. Registration may then be performed between the adjacent segmented surface data and the intraoperative surface data, where the adjacent volumetric fiducial points and adjacent intraoperative fiducial points are used to perform an initial registration, followed by a surface-to-surface registration, to obtain the per-level registration transform.

It is noted that the aforementioned method of generating adjacent intraoperative fiducial points is an approximation, and extending these fiducial points beyond the adjacent spinal level can lead to accumulation of errors. Accordingly, in one example implementation, the intraoperative fiducial points may be refined by using the per-level registration transform previously computed between the adjacent segmented surface data and the intraoperative surface data. In this example method, the intraoperative fiducials associated with the region associated with the pre-selected spinal level in the intraoperative frame of reference are first transformed into the volumetric frame of reference, using the per-level registration transform corresponding to the pre-selected spinal level. The inter-level transform is then used to further transform the position of these intraoperative fiducial points into the adjacent spinal level, in the volumetric frame of reference. As a further refinement, the transformed fiducial points are shifted so that they lie within the adjacent segmented surface data as previously described, analogous to the illustration in FIG. 10B. Finally, the fiducials points are transformed back into the intraoperative frame of reference using the per-level registration transform corresponding to the adjacent spinal level.

This method may be repeated to generate the intraoperative fiducial points for all of the relevant spinal levels (including the first spinal level and the second spinal level), thereby generating a set of per-level intraoperative fiducial points, where errors introduced by the use of the inter-level transforms are iteratively corrected both by using the inter-level registration transforms and snapping the points into the intraoperative surface, as described above.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing intraoperative registration between intraoperative surface data and pre-operative volumetric image data associated with a subject, the method comprising:
    employing an optical surface topography detection device to obtain intraoperative surface data characterizing at least a first surface region and a second surface region of the subject;
    processing the pre-operative volumetric image data to generate pre-operative surface data characterizing at least the first surface region and the second surface region of the subject;
    spatially segmenting one or both of the intraoperative surface data and the pre-operative surface data within the first surface region and the second surface region;
    performing registration between the intraoperative surface data and the pre-operative surface data, to obtain a first registration transform associated with the first surface region and a second registration transform associated with the second surface region; and
    intraoperatively generating and displaying navigation images by employing a selected registration transform to register the pre-operative volumetric image data to an intraoperative frame of reference, wherein the selected registration transform is dynamically and intraoperatively selected from at least the first registration transform and the second registration transform.

2. The method according to claim 1 wherein the selected registration transform is dynamically and intraoperatively selected according to a proximity of one or more tracked instruments relative to the first surface region and the second surface region.

3. The method according to claim 1 wherein the selected registration transform is dynamically and intraoperatively selected according to a proximity of a selected tracked instrument relative to the first surface region and the second surface region.

4. The method according to claim 1 wherein the selected registration transform is dynamically and intraoperatively selected according to a detected gaze direction of an operator.

5. The method according to claim 1 wherein the selected registration transform is dynamically and intraoperatively selected according to user input.

6. The method according to claim 5 wherein the user input comprises a selected location within the navigation images, and wherein the selected registration transform is dynamically and intraoperatively selected according to a proximity of the selected location relative to the first surface region and the second surface region.

7. The method according to claim 5 wherein the user input comprises a selection, within the navigation images, of one of the first surface region and the second surface region.

8. The method according to claim 1 wherein the first registration transform and the second registration transform are intraoperatively updated one or more times based on newly acquired intraoperative surface data.

9. The method according to claim 8 wherein the first registration transform and the second registration transform are intraoperatively updated according to an update interval of less than 10 seconds.

10. The method according to claim 8 wherein the first registration transform and the second registration transform are intraoperatively updated according to an update interval of less than 5 seconds.

11. The method according to claim 8 wherein the first registration transform and the second registration transform are intraoperatively updated according to an update interval of less than 1 second.

12. The method according to claim 8 further comprising employing a previous first registration transform and a previous second registration transform as initial estimates when updating the respective first registration transform and second registration transform based on the newly acquired intraoperative surface data.

13. The method according to claim 12 wherein the previous first registration transform and the previous second registration transform are only employed as initial estimates when registration quality measures associated with the registration between the pre-operative volumetric image data and the newly acquired intraoperative surface data satisfy pre-selected criteria.

14. The method according to claim 1 wherein the first surface region is proximal to a first planned surgical intervention location and the second surface region corresponds a second planned surgical intervention location.

15. The method according to claim 1 wherein the first surface region and the second surface region each comprise at least one respective anatomical surface feature.

16. The method according to claim 1 wherein the first surface region is associated with non-sterile phase of a surgical procedure, and the second surface region is associated with a sterile phase of the surgical procedure.

17. The method according to claim 1 wherein the intraoperative surface data is segmented proximal to the first surface region and the second surface region.

18. The method according to claim 1 wherein the pre-operative surface data is segmented proximal to the first surface region and the second surface region.

19. The method according to claim 18 wherein the first surface region corresponds to a first spinal level, and the second surface region corresponds to a second spinal level, and wherein segmented surface data and the volumetric fiducial points respectively associated therewith, are obtained by:
(i) obtaining input identifying at least three volumetric fiducial points at a pre-selected spinal level of a plurality of spinal levels within a volumetric frame of reference associated with the pre-operative volumetric image data, wherein the plurality of spinal levels includes the first spinal level and the second spinal level;
(ii) employing at least one of the volumetric fiducial points associated with the pre-selected spinal level to perform segmentation on the pre-operative surface data, thereby obtaining segmented surface data associated with the pre-selected spinal level;
(iii) employing the pre-selected spinal level as an initial spinal level when performing steps (iv) to (vi) for a first time;
(iv) determining an adjacent volumetric region, within the volumetric frame of reference, that is associated with an adjacent spinal level that is adjacent to the initial spinal level;
(v) performing segmentation on the pre-operative surface data within the adjacent volumetric region, thereby obtaining adjacent segmented surface data associated with the adjacent spinal level;
(vi) registering the segmented surface data associated with the initial spinal level to the adjacent segmented surface data, thereby obtaining an inter-level transform between the initial spinal level and the adjacent spinal level;
(vii) repeating steps (iv) to (vi) one or more times, each time using the previous adjacent level as the initial level, to generate segmented surface data and the inter-level transforms associated with additional spinal levels of the plurality of spinal levels on a first side of the pre-selected spinal level, such that each inter-level transform is between adjacent spinal levels;
(viii) repeating steps (iii) to (vii) if additional spinal levels of the plurality of spinal levels reside on the other side of the pre-selected spinal level; and
(ix) employing the inter-level transforms and the volumetric fiducial points associated with the pre-selected spinal level to obtain volumetric fiducial points associated with the plurality of spinal levels.

20. The method according to claim 19 wherein employing the inter-level transforms and the volumetric fiducial points associated with the pre-selected spinal level to obtain volumetric fiducial points associated with the plurality of spinal levels comprises:
(x) applying the inter-level transform between the pre-selected spinal level and an adjacent spinal level to the volumetric fiducial points associated with the pre-selected spinal level, thereby obtaining estimated volumetric fiducial locations associated with the adjacent spinal level;
(xi) employing the estimated volumetric fiducial locations to determine volumetric fiducial points residing within the segmented surface defined by the segmented surface data corresponding to the adjacent spinal level; and
(xii) repeating steps (x) and (xi) to determine the volumetric fiducial points associated with the additional spinal levels of the plurality of spinal levels.

21. The method according to claim 19 wherein intraoperative fiducial points associated with the first spinal level and the second spinal level are generated by:
obtaining input identifying at least three intraoperative fiducial points at a selected spinal level within an intraoperative frame of reference, wherein the selected spinal level in the intraoperative frame of reference is expected to correspond to the pre-selected spinal level in the volumetric frame of reference, and wherein the intraoperative fiducial points at the pre-selected spinal level correspond to the volumetric fiducial points at the pre-selected spinal level; and
employing the inter-level transforms and the intraoperative fiducial points associated with the selected spinal level to obtain intraoperative fiducial points associated with the other spinal levels of the plurality of spinal levels.

22. The method according to claim 21 wherein employing the inter-level transforms and the intraoperative fiducial points associated with the selected spinal level to obtain intraoperative fiducial points associated with the other spinal levels of the plurality of spinal levels comprises:
(x) employing the registration transform between the pre-selected spinal level and the selected spinal level to transform the intraoperative fiducial points associated with the selected spinal level into the volumetric frame of reference, thereby obtaining transformed intraoperative fiducial points;

(xi) applying the inter-level transform between the preselected spinal level and the adjacent spinal level to the transformed intraoperative fiducial points, thereby obtaining estimated adjacent fiducial locations associated with the adjacent spinal level;

(xi) employing the estimated adjacent fiducial locations to determine transformed adjacent fiducial points residing within the segmented surface data associated with the adjacent spinal level;

(xii) employing the registration transform associated with the adjacent spinal level to transform the transformed adjacent fiducial points into the intraoperative frame of reference, thereby obtaining intraoperative fiducial points associated with the adjacent spinal level; and (xiii) repeating steps (x) and (xii) to determine the intraoperative fiducial points associated with the additional spinal levels of the plurality of spinal levels.

23. The method according to claim 1 wherein the first registration transform and the second registration transform are calculated based on:
selection, by an operator, of pre-operative fiducial locations within the first surface region and the second surface region of the pre-operative surface data; and
intraoperative identification of intraoperative fiducial locations within the first surface region and the second surface region.

24. A method of performing intraoperative registration between a subject and pre-operative volumetric image data associated with the subject, the method comprising:
employing an optical surface topography detection device to obtain intraoperative surface data characterizing at least a first surface region and a second surface region of the subject;
processing the pre-operative volumetric image data to generate pre-operative surface data characterizing at least the first surface region and the second surface region of the subject;
spatially segmenting one or both of the intraoperative surface data and the pre-operative surface data within the first surface region and the second surface region;
performing registration between the intraoperative surface data and the pre-operative surface data to obtain a first registration transform associated with the first surface region and a second registration transform associated with the second surface region; and
intraoperatively generating and displaying first navigation images and second navigation images in two different windows of a user interface, wherein the first navigation images are generated by employing the first registration transform to register the pre-operative volumetric image data to an intraoperative frame of reference, and the second navigation images are generated by employing the second registration transform to register the pre-operative volumetric image data to the intraoperative frame of reference.

25. A system for performing intraoperative registration between intraoperative surface data and pre-operative volumetric image data associated with a subject, the system comprising:
an optical surface topography detection subsystem; and
computer hardware operatively coupled to said optical surface topography detection subsystem, wherein said computer hardware comprises memory coupled with one or more processors to store instructions, which when executed by the one or more processors, causes the one or more processors to perform operations comprising:
controlling said optical surface topography detection subsystem to obtain intraoperative surface data characterizing at least a first surface region and a second surface region of the subject;
processing the pre-operative volumetric image data to generate pre-operative surface data characterizing at least the first surface region and the second surface region of the subject;
spatially segmenting one or both of the intraoperative surface data and the pre-operative surface data within the first surface region and the second surface region;
performing registration between the intraoperative surface data and the pre-operative surface data to obtain a first registration transform associated with the first surface region and a second registration transform associated with the second surface region; and
intraoperatively generating and displaying navigation images by employing a selected registration transform to register the pre-operative volumetric image data to an intraoperative frame of reference, wherein the selected registration transform is dynamically and intraoperatively selected from at least the first registration transform and the second registration transform.

26. The system according to claim 25 wherein the computer hardware is configured such that the selected registration transform is dynamically and intraoperatively selected according to a proximity of one or more tracked instruments relative to the first surface region and the second surface region.

27. The system according to claim 25 wherein the computer hardware is configured such that the selected registration transform is dynamically and intraoperatively selected according to a proximity of a selected tracked instrument relative to the first surface region and the second surface region.

28. The system according to claim 25 wherein the computer hardware is configured such that the selected registration transform is dynamically and intraoperatively selected according to a detected gaze direction of an operator.

29. The system according to claim 25 wherein the computer hardware is configured such that the selected registration transform is dynamically and intraoperatively selected according to user input.

30. The system according to claim 29 wherein the computer hardware is configured such that the user input comprises a selected location within the navigation images, and wherein the selected registration transform is dynamically and intraoperatively selected according to a proximity of the selected location relative to the first surface region and the second surface region.

31. The system according to claim 29 wherein the computer hardware is configured such that the user input comprises a selection, within the navigation images, of one of the first surface region and the second surface region.

32. The system according to claim 25 wherein the computer hardware is configured such that the first registration transform and the second registration transform are intraoperatively updated one or more times based on newly acquired intraoperative surface data.

33. The system according to claim 32 wherein the computer hardware is configured such that the first registration transform and the second registration transform are intraoperatively updated according to an update interval of less than 10 seconds.

34. The system according to claim 32 wherein the computer hardware is configured such that the first registration transform and the second registration transform are intraoperatively updated according to an update interval of less than 5 seconds.

35. The system according to claim 32 wherein the computer hardware is configured such that the first registration transform and the second registration transform are intraoperatively updated according to an update interval of less than 1 second.

36. The system according to claim 32 the computer hardware is configured such that a previous first registration transform and a previous second registration transform are employed as initial estimates when updating the respective first registration transform and second registration transform based on the newly acquired intraoperative surface data.

37. The system according to claim 36 wherein the computer hardware is configured such that the previous first registration transform and the previous second registration transform are only employed as initial estimates when registration quality measures associated with the registration between the pre-operative volumetric image data and the newly acquired intraoperative surface data satisfy pre-selected criteria.

38. The system according to claim 25 wherein the computer hardware is configured such that the intraoperative surface data is segmented proximal to the first surface region the second surface region.

39. The system according to claim 25 wherein the computer hardware is configured such that the pre-operative surface data is segmented proximal to the first surface region and the second surface region.

40. The system according to claim 39 wherein the computer hardware is configured such that the first surface region corresponds to a first spinal level, and the second surface region corresponds to a second spinal level, and wherein segmented surface data, and volumetric fiducial points respectively associated therewith, are obtained by:
(i) obtaining input identifying at least three volumetric fiducial points at a pre-selected spinal level of a plurality of spinal levels within a volumetric frame of reference associated with the pre-operative volumetric image data, wherein the plurality of spinal levels includes the first spinal level and the second spinal level;
(ii) employing at least one of the volumetric fiducial points associated with the pre-selected spinal level to perform segmentation on the pre-operative surface data, thereby obtaining segmented surface data associated with the pre-selected spinal level;
(iii) employing the pre-selected spinal level as an initial spinal level when performing steps (iv) to (vi) for a first time;
(iv) determining an adjacent volumetric region, within the volumetric frame of reference, that is associated with an adjacent spinal level that is adjacent to the initial spinal level;
(v) performing segmentation on the pre-operative surface data within the adjacent volumetric region, thereby obtaining adjacent segmented surface data associated with the adjacent spinal level;
(vi) registering the segmented surface data associated with the initial spinal level to the adjacent segmented surface data, thereby obtaining an inter-level transform between the initial spinal level and the adjacent spinal level;
(vii) repeating steps (iv) to (vi) one or more times, each time using the previous adjacent level as the initial level, to generate segmented surface data and the inter-level transforms associated with additional spinal levels of the plurality of spinal levels on a first side of the pre-selected spinal level, such that each inter-level transform is between adjacent spinal levels;
(viii) repeating steps (iii) to (vii) if additional spinal levels of the plurality of spinal levels reside on the other side of the pre-selected spinal level; and
(ix) employing the inter-level transforms and the volumetric fiducial points associated with the pre-selected spinal level to obtain volumetric fiducial points associated with the plurality of spinal levels.

41. The system according to claim 40 wherein the computer hardware is configured such that employing the inter-level transforms and the volumetric fiducial points associated with the pre-selected spinal level to obtain volumetric fiducial points associated with the plurality of spinal levels comprises:
(x) applying the inter-level transform between the pre-selected spinal level and an adjacent spinal level to the volumetric fiducial points associated with the pre-selected spinal level, thereby obtaining estimated volumetric fiducial locations associated with the adjacent spinal level;
(xi) employing the estimated volumetric fiducial locations to determine volumetric fiducial points residing within the segmented surface defined by the segmented surface data corresponding to the adjacent spinal level; and
(xii) repeating steps (x) and (xi) to determine the volumetric fiducial points associated with the additional spinal levels of the plurality of spinal levels.

42. The system according to claim 40 wherein the computer hardware is configured such that intraoperative fiducial points associated with the first spinal level and the second spinal level are generated by:
obtaining input identifying at least three intraoperative fiducial points at a selected spinal level within an intraoperative frame of reference, wherein the selected spinal level in the intraoperative frame of reference is expected to correspond to the pre-selected spinal level in the volumetric frame of reference, and wherein the intraoperative fiducial points at the pre-selected spinal level correspond to the volumetric fiducial points at the pre-selected spinal level; and
employing the inter-level transforms and the intraoperative fiducial points associated with the selected spinal level to obtain intraoperative fiducial points associated with the other spinal levels of the plurality of spinal levels.

43. The system according to claim 42 wherein the computer hardware is configured such that employing the inter-level transforms and the intraoperative fiducial points associated with the selected spinal level to obtain intraoperative fiducial points associated with the other spinal levels of the plurality of spinal levels comprises:
(x) employing the registration transform between the pre-selected spinal level and the selected spinal level to transform the intraoperative fiducial points associated with the selected spinal level into the volumetric frame of reference, thereby obtaining transformed intraoperative fiducial points;
(xi) applying the inter-level transform between the pre-selected spinal level and the adjacent spinal level to the transformed intraoperative fiducial points, thereby obtaining estimated adjacent fiducial locations associated with the adjacent spinal level;

(xi) employing the estimated adjacent fiducial locations to determine transformed adjacent fiducial points residing within the segmented surface data associated with the adjacent spinal level;

(xii) employing the registration transform associated with the adjacent spinal level to transform the transformed adjacent fiducial points into the intraoperative frame of reference, thereby obtaining intraoperative fiducial points associated with the adjacent spinal level; and (xiii) repeating steps (x) and (xii) to determine the intraoperative fiducial points associated with the additional spinal levels of the plurality of spinal levels.

44. The system according to claim 25 wherein the computer hardware is configured such that the first registration transform and the second registration transform are calculated based on:
  selection, by an operator, of pre-operative fiducial locations within the first surface region and the second surface region of the pre-operative surface data; and
  intraoperative identification of intraoperative fiducial locations within the first surface region and the second surface region.

45. A system of performing intraoperative registration between a subject and pre-operative volumetric image data associated with the subject, the system comprising:
  an optical surface topography detection subsystem; and
  computer hardware operatively coupled to said optical surface topography detection subsystem, wherein said computer hardware comprises memory coupled with one or more processors to store instructions, which when executed by the one or more processors, causes the one or more processors to perform operations comprising:
  controlling the optical surface topography detection subsystem to obtain intraoperative surface data characterizing at least a first surface region and a second surface region of the subject;
  processing the pre-operative volumetric image data to generate pre-operative surface data characterizing at least the first surface region and the second surface region of the subject;
  spatially segmenting one or both of the intraoperative surface data and the pre-operative surface data within the first surface region and the second surface region;
  performing registration between the intraoperative surface data and the pre-operative surface data to obtain a first registration transform associated with the first surface region and a second registration transform associated with the second surface region; and
  intraoperatively generating and displaying first navigation images and second navigation images in two different windows of a user interface, wherein the first navigation images are generated by employing the first registration transform to register the pre-operative volumetric image data to an intraoperative frame of reference, and the second navigation images are generated by employing the second registration transform to register the pre-operative volumetric image data to the intraoperative frame of reference.

* * * * *

UNITED STATES PATENT AND TRADEMARK OFFICE
CERTIFICATE OF CORRECTION

PATENT NO. : 11,712,304 B2
APPLICATION NO. : 16/623649
DATED : August 1, 2023
INVENTOR(S) : Michael K. K. Leung et al.

It is certified that error appears in the above-identified patent and that said Letters Patent is hereby corrected as shown below:

In the Claims

Please amend Claim 22 as indicated:
22. The method according to claim 21 wherein employing the inter-level transforms and the intraoperative fiducial points associated with the selected spinal level to obtain intraoperative fiducial points associated with the other spinal levels of the plurality of spinal levels comprises:
(x) employing the registration transform between the pre-selected spinal level and the selected spinal level to transform the intraoperative fiducial points associated with the selected spinal level into the volumetric frame of reference, thereby obtaining transformed intraoperative fiducial points;
(xi) applying the inter-level transform between the pre- selected spinal level and the adjacent spinal level to the transformed intraoperative fiducial points, thereby obtaining estimated adjacent fiducial locations associated with the adjacent spinal level;
(xii) employing the estimated adjacent fiducial locations to determine transformed adjacent fiducial points residing within the segmented surface data associated with the adjacent spinal level;
(xiii) employing the registration transform associated with the adjacent spinal level to transform the transformed adjacent fiducial points into the intraoperative frame of reference, thereby obtaining intraoperative fiducial points associated with the adjacent spinal level; and
(xiv) repeating steps (x) and (xii) to determine the intra- operative fiducial points associated with the additional spinal levels of the plurality of spinal levels.

Please amend Claim 43 as indicated:
43. The system according to claim 42 wherein the computer hardware is configured such that employing the inter-level transforms and the intraoperative fiducial points associated with the selected spinal level to obtain intraoperative fiducial points associated with the other spinal levels of the plurality of spinal levels comprises:
(x) employing the registration transform between the pre-selected spinal level and the selected spinal level to transform the intraoperative fiducial points associated with the selected spinal level into the volumetric frame of reference, thereby obtaining transformed intraoperative fiducial points;

Signed and Sealed this
Twenty-third Day of January, 2024

Katherine Kelly Vidal
*Director of the United States Patent and Trademark Office*

(xi) applying the inter-level transform between the pre-selected spinal level and the adjacent spinal level to the transformed intraoperative fiducial points, thereby obtaining estimated adjacent fiducial locations associated with the adjacent spinal level;

(xii) employing the estimated adjacent fiducial locations to determine transformed adjacent fiducial points residing within the segmented surface data associated with the adjacent spinal level;

(xiii) employing the registration transform associated with the adjacent spinal level to transform the transformed adjacent fiducial points into the intraoperative frame at reference, thereby obtaining intraoperative fiducial points associated with the adjacent spinal level; and (xiv) repeating steps (x) and (xii) to determine the intra-operative fiducial points associated with the additional spinal levels of the plurality of spinal levels.